US011666294B2

(12) United States Patent
Makino et al.

(10) Patent No.: US 11,666,294 B2
(45) Date of Patent: Jun. 6, 2023

(54) MOBILE RADIOGRAPHIC IMAGING APPARATUS, OPERATION METHOD OF MOBILE RADIOGRAPHIC IMAGING APPARATUS, AND OPERATION PROGRAM OF MOBILE RADIOGRAPHIC IMAGING APPARATUS

(71) Applicant: FUJIFILM Corporation, Tokyo (JP)

(72) Inventors: Kazuhiro Makino, Kanagawa (JP); Ryo Imamura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 418 days.

(21) Appl. No.: 16/698,983

(22) Filed: Nov. 28, 2019

(65) Prior Publication Data

US 2020/0170595 A1 Jun. 4, 2020

(30) Foreign Application Priority Data

Nov. 30, 2018 (JP) .............................. JP2018-225682

(51) Int. Cl.
*A61B 6/00* (2006.01)

(52) U.S. Cl.
CPC ............ *A61B 6/4405* (2013.01); *A61B 6/548* (2013.01); *A61B 2560/0431* (2013.01); *A61B 2560/0437* (2013.01); *A61B 2562/02* (2013.01)

(58) Field of Classification Search
CPC .... A61B 2560/0431; A61B 2560/0437; A61B 2562/02; A61B 6/105; A61B 6/102;
(Continued)

(56) References Cited

U.S. PATENT DOCUMENTS 7,309,159 B2    12/2007   Watanabe
7,643,613 B2     1/2010   Watanabe
(Continued)

FOREIGN PATENT DOCUMENTS

JP    2000201914    7/2000
JP    2006141669    6/2006
(Continued)

OTHER PUBLICATIONS

English translation of JP2006141669 (Year: 2006).*
"Office Action of Japan Counterpart Application" with English translation thereof, dated Feb. 15, 2022, p. 1-p. 8.

*Primary Examiner* — Dani Fox
*Assistant Examiner* — Soorena Kefayati
(74) *Attorney, Agent, or Firm* — JCIPRNET

(57) ABSTRACT

A first acquisition unit acquires the current position of a carriage unit as information regarding the travel environment of the carriage unit. A second acquisition unit acquires a first upper limit value of the travel speed as appropriate travel conditions of the carriage unit corresponding to the current position acquired by the first acquisition unit. A third acquisition unit acquires a first measurement value of the travel speed as information regarding the travel state of the carriage unit. A travel state correction controller performs travel state correction control to make a correction to a travel state satisfying the appropriate travel conditions in a case where the travel state acquired by the third acquisition unit deviates from the appropriate travel conditions acquired by the second acquisition unit. That is, the travel state correction controller reduces the travel speed of the carriage unit in a case where the first measurement value exceeds the first upper limit value.

9 Claims, 32 Drawing Sheets

(58) Field of Classification Search
CPC ......... A61B 6/104; A61B 6/10; A61B 6/4405; A61B 6/547; A61B 6/548
See application file for complete search history.

(56) References Cited

U.S. PATENT DOCUMENTS

| | | | | |
|---|---|---|---|---|
| 2001/0044577 | A1* | 11/2001 | Braun | G05D 1/0265 600/417 |
| 2006/0120512 | A1* | 6/2006 | Watanabe | A61B 6/10 378/198 |
| 2014/0369477 | A1* | 12/2014 | Okuno | A61B 6/4405 378/193 |
| 2015/0331425 | A1* | 11/2015 | Chen | G05D 1/0246 701/25 |
| 2016/0066869 | A1* | 3/2016 | Haider | A61B 6/0407 128/845 |
| 2016/0287193 | A1* | 10/2016 | Katsumata | A61B 6/4405 |
| 2017/0303882 | A1* | 10/2017 | Ficarra | A61B 6/44 |
| 2017/0347979 | A1* | 12/2017 | Fehre | G06F 30/13 |
| 2018/0021003 | A1* | 1/2018 | Kim | A61B 6/584 378/189 |
| 2018/0031377 | A1* | 2/2018 | Guo | G05D 1/024 |
| 2018/0160992 | A1* | 6/2018 | Shirota | A61B 6/4452 |
| 2018/0242932 | A1* | 8/2018 | Sullivan | A61B 6/027 |
| 2018/0321684 | A1* | 11/2018 | Gao | B60B 19/003 |
| 2019/0209104 | A1* | 7/2019 | Dirauf | A61B 6/4405 |
| 2020/0016927 | A1* | 1/2020 | Dietrich | A61B 50/13 |

FOREIGN PATENT DOCUMENTS

| | | |
|---|---|---|
| JP | 2006141669 A * | 6/2006 |
| JP | 2006158508 | 6/2006 |
| JP | 2007044136 | 2/2007 |
| JP | 2009178361 | 8/2009 |
| JP | 2010082317 | 4/2010 |
| JP | 2010094162 | 4/2010 |
| JP | 2010207393 | 9/2010 |
| JP | 2017006345 | 1/2017 |

* cited by examiner

FIG. 10

| 11.13.2018 THIRD FLOOR RADIOGRAPHIC IMAGING SCHEDULE | | | |
|---|---|---|---|
| PATIENT ID | PATIENT NAME | PATIENT ROOM | IMAGING PART |
| P0001 | TARO FUJI | 302 | CHEST |
| P0005 | HARUKO YAMADA | 305 | CHEST |
| P0020 | KAZUO SUZUKI | 305 | CHEST |
| P0050 | DAISUKE TANAKA | 307 | CHEST |

| POSITION | APPROPRIATE TRAVEL CONDITIONS (FIRST UPPER LIMIT VALUE OF TRAVEL SPEED) | CAUSE OF SETTING |
|---|---|---|
| ELEVATOR HALL | 1.0 km/h | NUMBER OF OBSTACLES |
| SLOPE 1, 2 (IN CASE OF DOWNHILL) | 1.5 km/h | INCLINATION STATE |
| CORRIDOR 1,2,4,5 | 3.0 km/h | WIDTH |
| PROTRUDING PORTION 1, 2 | 1.5 km/h | UNEVENNESS STATE |
| CORNER 1, 2 | 1.0 km/h | CORNER |
| CORRIDOR 3 | 1.5 km/h | WIDTH |

| POSITION | TIME ZONE | APPROPRIATE TRAVEL CONDITIONS (FIRST UPPER LIMIT VALUE OF TRAVEL SPEED) |
|---|---|---|
| ELEVATOR HALL | 9:00 TO 18:00 | 1.0 km/h |
| | AFTER 18:00 | 3.0 km/h |
| SLOPE 1, 2 (IN CASE OF DOWNHILL) | | 1.5 km/h |
| CORRIDOR 1,2,4,5 | | 3.0 km/h |
| PROTRUDING PORTION 1, 2 | | 1.5 km/h |
| CORNER 1, 2 | | 1.0 km/h |
| CORRIDOR 3 | | 1.5 km/h |

FIG. 21

| TRAVEL ENVIRONMENT | APPROPRIATE TRAVEL CONDITIONS (SECOND UPPER LIMIT VALUE OF TRAVEL SPEED) | CAUSE OF SETTING |
|---|---|---|
| TRAVEL PASSAGE WIDTH LESS THAN 2.1 m | 1.5 km/h | WIDTH |
| TRAVEL PASSAGE WIDTH OF 2.1 m OR MORE | 3.0 km/h | WIDTH |
| CORNER | 1.0 km/h | CORNER |
| THERE IS OBSTACLE | 1.0 km/h | NUMBER OF OBSTACLES |
| DISTANCE of 3 m FROM OBSTACLE | 1.0 km/h | DISTANCE FROM OBSTACLE |
| DISTANCE OF 2 m FROM OBSTACLE | 0.8 km/h | DISTANCE FROM OBSTACLE |
| DISTANCE OF 1 m FROM OBSTACLE | 0.5 km/h | DISTANCE FROM OBSTACLE |
| THERE IS DOWNHILLSLOPE IN TRAVEL PASSAGE | 1.5 km/h | INCLINATION STATE |
| THERE IS UNEVENNESS IN TRAVEL PASSAGE | 1.5 km/h | UNEVENNESS STATE |

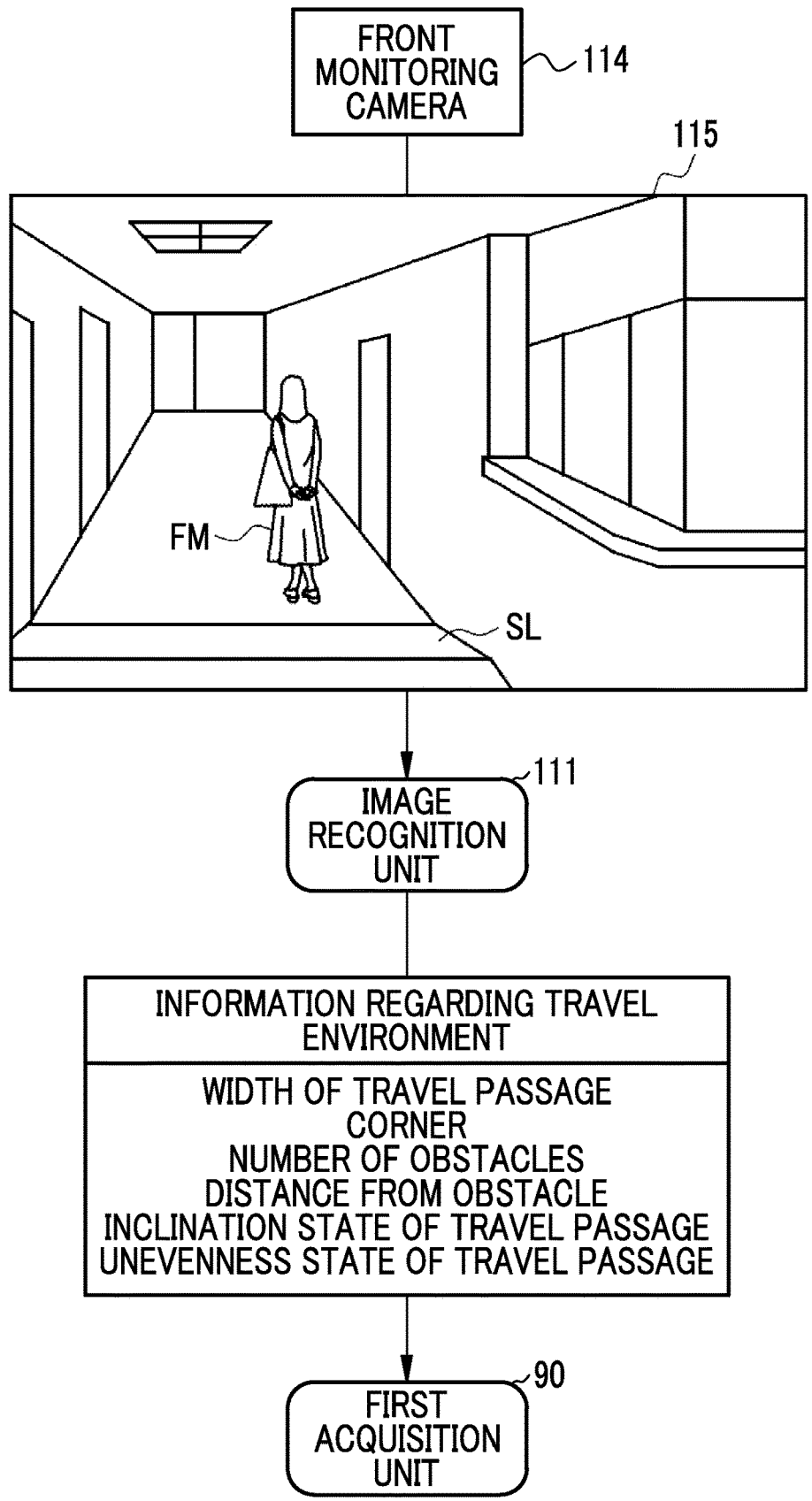

MOBILE RADIOGRAPHIC IMAGING APPARATUS, OPERATION METHOD OF MOBILE RADIOGRAPHIC IMAGING APPARATUS, AND OPERATION PROGRAM OF MOBILE RADIOGRAPHIC IMAGING APPARATUS

CROSS-REFERENCE TO RELATED APPLICATIONS

The present application claims priority under 35 U.S.C. § 119 to Japanese Patent Application No., 2018-225682 filed on Nov. 30, 2018. The above application is hereby expressly incorporated by reference, in its entirety, into the present application.

BACKGROUND

1. Technical Field

The technique of the present disclosure relates to a mobile radiographic imaging apparatus, an operation method of a mobile radiographic imaging apparatus, and an operation program of a mobile radiographic imaging apparatus.

2. Description of the Related Art

A mobile radiographic imaging apparatus that performs radiographic imaging while going around a patient room in a hospital is known. The mobile radiographic imaging apparatus comprises a carriage unit and a handle. The carriage unit has a plurality of wheels for traveling. The handle is gripped by an operator, such as a radiology technician, in order to steer the carriage unit. The operator controls the travel speed and travel direction of the carriage unit by operating the handle to change the way in which the force is applied to the handle or to adjust the direction in which the force is applied to the handle. Hereinafter, a travel mode in which the carriage unit travels by the operation of the operator on the handle will be referred to as manual travel.

A mobile radiographic imaging apparatus described in JP2010-082317A has a wheel driving unit, such as a motor that rotationally drives wheels of a carriage unit, and assists manual travel by the wheel driving unit. Then, the driving conditions of the carriage unit, such as the assist force of the wheel driving unit, are stored for each operator, and the driving conditions are changed for each operator.

SUMMARY

As described above, in manual travel, the travel speed and the travel direction of the carriage unit are controlled by the operator. For this reason, there are operators who make the carriage unit travel at a relatively high travel speed regardless of the travel environment of the carriage unit, and there are operators who make the carriage unit meander without the travel direction being fixed for reasons, such as having a baggage in one hand. Therefore, there has been concern from the viewpoint of ensuring higher safety of manual travel.

It is an object of the technique of the present disclosure to provide a mobile radiographic imaging apparatus, an operation method of a mobile radiographic imaging apparatus, and an operation program of a mobile radiographic imaging apparatus capable of realizing the safer manual travel.

In order to achieve the aforementioned object, a mobile radiographic imaging apparatus of the present disclosure comprises: a carriage unit which has wheels for traveling and on which a main body unit is mounted; a handle that is provided in the main body unit to steer the carriage unit; a wheel driving unit that rotationally drives the wheels to assist manual travel for making the carriage unit travel by an operator's operation on the handle; a first acquisition unit that acquires information regarding a travel environment of the carriage unit; a second acquisition unit that acquires appropriate travel conditions of the carriage unit according to the information regarding the travel environment acquired by the first acquisition unit; a third acquisition unit that acquires information regarding a travel state of the carriage unit in the manual travel; and a travel state correction controller that per forms travel state correction control to make a correction to a travel state satisfying the appropriate travel conditions by controlling the wheel driving unit in a case where the travel state acquired by the third acquisition unit deviates from the appropriate travel conditions acquired by the second acquisition unit.

It is preferable that the appropriate travel conditions are stored in a storage unit so as to be associated with each of a plurality of positions set in advance on a floor on which the carriage unit manually travels, the first acquisition unit acquires a current position of the carriage unit on the floor as the information regarding the travel environment, and the second acquisition unit reads and acquires the appropriate travel conditions corresponding to the current position acquired by the first acquisition unit from the storage unit.

It is preferable that the second acquisition unit acquires, as the appropriate travel conditions, a first upper limit value of a travel speed of the carriage unit corresponding to at least one of a width of a travel passage of the carriage unit, whether or not the travel passage is a corner, the number of obstacles that are present in the travel passage to become obstacles to the manual travel, an inclination state of the travel passage, or an unevenness state of the travel passage. It is preferable that the third acquisition unit acquires a first measurement value of the travel speed of the carriage unit as the information regarding the travel state and that the travel state correction controller performs the travel state correction control in a case where the first measurement value acquired by the third acquisition unit exceeds the first upper limit value acquired by the second acquisition unit.

It is preferable that the first upper limit value according to the number of obstacles is set for each time zone.

It is preferable that the first acquisition unit acquires the information regarding the travel environment based on a detection result of a detection sensor that detects the travel environment.

It is preferable that the first acquisition unit acquires at least one of a width of a travel passage of the carriage unit, whether or not the travel passage is a corner, the number of obstacles that are present in the travel passage to become obstacles to the manual travel, a distance from each of the obstacles, an inclination state of the travel passage, or an unevenness state of the travel passage, as the information regarding the travel environment, based on the detection result.

It is preferable that the second acquisition unit acquires a second upper limit value of a travel speed of the carriage unit as the appropriate travel conditions, the third acquisition unit acquires a second measurement value of the travel speed of the carriage unit as the information regarding the travel state, and the travel state correction controller performs the travel state correction control in a case where the second measurement value acquired by the third acquisition unit exceeds the second upper limit value acquired by the second acquisition unit.

It is preferable that the second acquisition unit acquires an upper limit value of a meandering amount of the carriage unit as the appropriate travel conditions, the third acquisition unit acquires a measurement value of the meandering amount of the carriage unit as the information regarding the travel state, and the travel state correction controller performs the travel state correction control in a case where the measurement value of the meandering amount acquired by the third acquisition unit exceeds the upper limit value of the meandering amount acquired by the second acquisition unit.

It is preferable to further comprise a display controller that performs control to provide notification of a cause of performing the travel state correction control.

An operation method of a mobile radiographic imaging apparatus of the present disclosure is an operation method of a mobile radiographic imaging apparatus comprising a carriage unit which has wheels for traveling and on which a main body unit is mounted, a handle that is provided in the main body unit to steer the carriage unit, and a wheel driving unit that rotationally drives the wheels to assist manual travel for making the carriage unit travel by an operator's operation on the handle. The method comprises: a first acquisition step of acquiring information regarding a travel environment of the carriage unit; a second acquisition step of acquiring appropriate travel conditions of the carriage unit according to the information regarding the travel environment acquired in the first acquisition step; a third acquisition step of acquiring information regarding a travel state of the carriage unit in the manual travel; and a travel state correction control step of performing travel state correction control to make a correction to a travel state satisfying the appropriate travel conditions by controlling the wheel driving unit in a case where the travel state acquired in the third acquisition step deviates from the appropriate travel conditions acquired in the second acquisition unit.

An operation program of a mobile radiographic imaging apparatus of the present disclosure is an operation program of a mobile radiographic imaging apparatus comprising a carriage unit which has wheels for traveling and on which a main body unit is mounted, a handle that is provided in the main body unit to steer the carriage unit, and a wheel driving unit that rotationally drives the wheels to assist manual travel for making the carriage unit travel by an operator's operation on the handle. The operation program causes a computer to function as: a first acquisition unit that acquires information regarding a travel environment of the carriage unit; a second acquisition unit that acquires appropriate travel conditions of the carriage unit according to the information regarding the travel environment acquired by the first acquisition unit; a third acquisition unit that acquires information regarding a travel state of the carriage unit in the manual travel; and a travel state correction controller that performs travel state correction control to make a correction to a travel state satisfying the appropriate travel conditions by controlling the wheel driving unit in a case where the travel state acquired by the third acquisition unit deviates from the appropriate travel conditions acquired by the second acquisition unit.

According to the technique of the present disclosure, it is possible to provide a mobile radiographic imaging apparatus, an operation method of a mobile radiographic imaging apparatus, and an operation program of a mobile radiographic imaging apparatus capable of realizing the safer manual travel.

BRIEF DESCRIPTION OF THE DRAWINGS

Exemplary embodiments according to the technique of the present disclosure will be described in detail based on the following figures, wherein:

FIG. 10 is a diagram showing an example of imaging schedule information;

FIG. 11 is a diagram showing an example of an appropriate travel conditions table;

FIG. 17A shows a case where the current position is a position where there are many people coming and going, and FIG. 17B shows a case where the current position is a narrow passage;

FIG. 19 is a diagram showing an appropriate travel conditions table in which a first upper limit value according to the number of obstacles is set for each time zone;

FIG. 21 is a diagram showing an appropriate travel conditions table of the second embodiment;

FIG. 22 is a diagram showing how information regarding a travel environment image-recognized from an image of a front monitoring camera is acquired by a first acquisition unit;

DETAILED DESCRIPTION

First Embodiment

Figure 1:
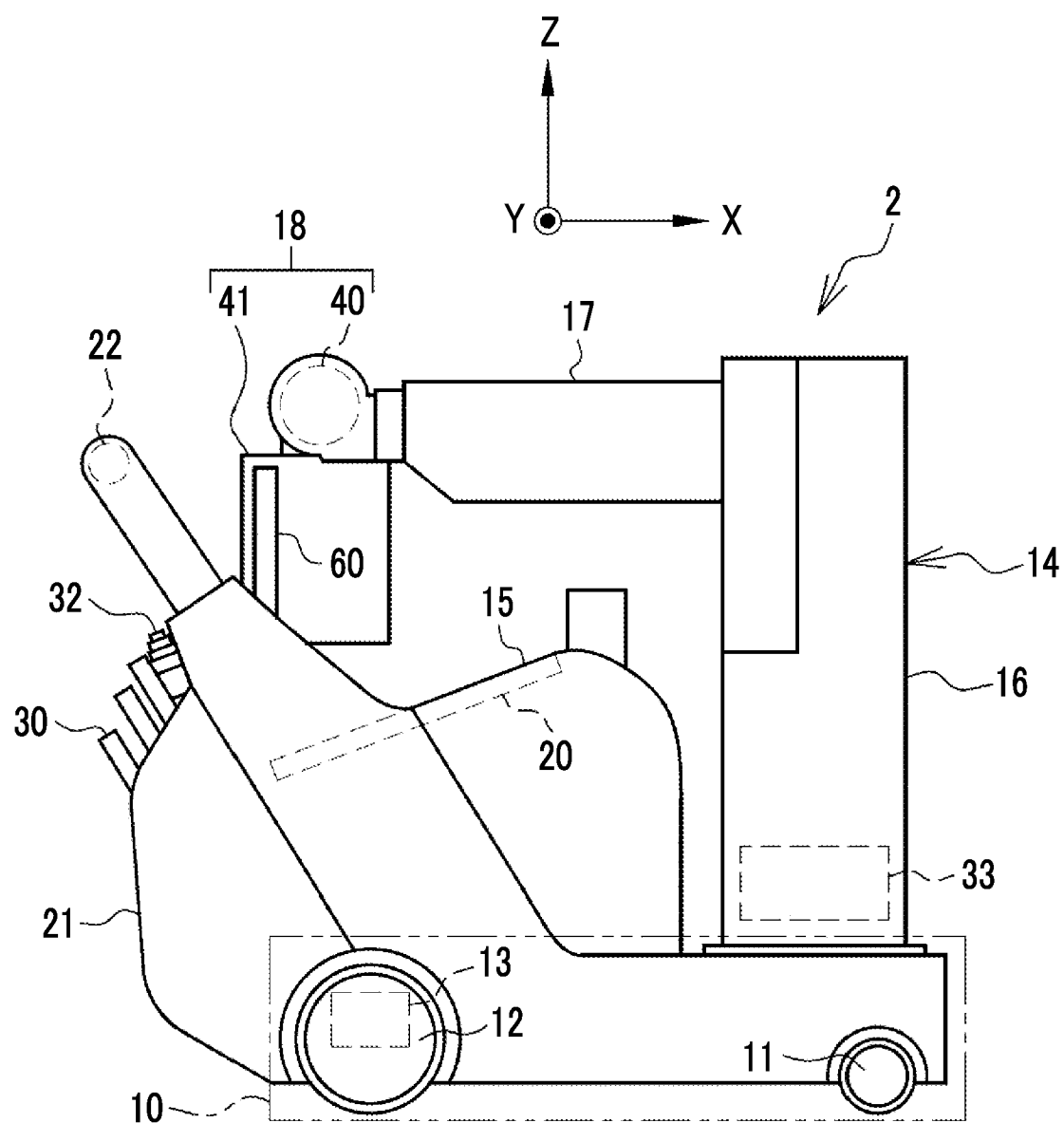
FIG. 1 is a diagram showing a mobile radiographic imaging apparatus.

In FIG. 1, a mobile radiographic imaging apparatus 2 comprises a carriage unit 10. The carriage unit 10 has a front wheel 11, a rear wheel 12, and a rear wheel driving unit 13. The front wheel 11 and the rear wheel 12 are examples of "wheels" according to the technique of the present disclosure. The rear wheel driving unit 13 is an example of a "wheel driving unit" according to the technique of the present disclosure.

The front wheel 11 is a pair of left and right casters that revolve around the Z axis indicating the height direction of the mobile radiographic imaging apparatus 2. The rear wheel 12 is also a pair of left and right like the front wheel 11, but does not revolve around the Z axis. However, the rear wheel 12 is rotated around the Y axis indicating the width direction of the mobile radiographic imaging apparatus 2 by the rear wheel driving unit 13. The front wheel 11 rotates following the rotation of the rear wheel 12. That is, the carriage unit 10 has four wheels and is of a rear wheel drive type. The carriage unit 10 is not limited to the rear wheel drive type, and may be of a front wheel drive type in which the front wheel 11 rotates around the Y axis by a front wheel driving unit. Alternatively, the carriage unit 10 may be an all-wheel drive type in which the front wheel 11 rotates around the Y axis by the front wheel driving unit and the rear wheel 12 rotates around the Y axis by the rear wheel driving unit.

The rear wheel driving unit 13 is two motors connected to the left and right rear wheels 12. The rear wheel driving unit 13 rotates the left and right rear wheels 12 independently of each other. For this reason, in a case where the rotation speed of the right rear wheel 12 is made faster than that of the left rear wheel 12 by the rear wheel driving unit 13, the mobile radiographic imaging apparatus 2 turns to the left. On the other hand, in a case where the rotation speed of the left rear wheel 12 is made faster than that of the right rear wheel 12 by the rear wheel driving unit 13, the mobile radiographic imaging apparatus 2 turns to the right.

The mobile radiographic imaging apparatus 2 can be moved in the hospital by the carriage unit 10. The mobile radiographic imaging apparatus 2 is used for so-called round-visit imaging in which radiographic imaging is performed while going around a patient room. For this reason, the mobile radiographic imaging apparatus 2 is also called a round-visit car. In addition, the mobile radiographic imaging apparatus 2 can also be brought into the operating room to perform radiographic imaging in the midst of surgery.

A main body unit 14 is mounted on the carriage unit 10. A central unit 15, a column unit 16, an arm unit 17, an irradiation unit 18, and the like are mounted in the main body unit 14. The mobile radiographic imaging apparatus 2 is moved in a state shown in FIG. 1 in which the irradiation unit 18 is housed in the upper portion of the central unit 15.

The central unit 15 has a console 20, a cassette housing unit 21, and a handle 22. The console 20 is embedded on the inclined upper surface of the central unit 15. The console 20 is configured to include an operation console 25 and a display 26 (refer to FIG. 5). The operation console 25 is operated by an operator OP at the time of setting the irradiation conditions and the like. The display 26 displays various screens including an irradiation conditions setting screen, a radiographic image, and the like.

The cassette housing unit 21 is disposed on the back surface of the central unit 15. An electronic cassette 30 is housed in the cassette housing unit 21. As is well known, the electronic cassette 30 is a radiographic image detector that detects a radiographic image expressed by an electrical signal based on radiation transmitted through a subject, and is a portable radiographic image detector capable of performing wireless communication using a built-in battery. There are a plurality of types of electronic cassettes 30 having vertical and horizontal sizes of 17 inches×17 inches, 17 inches×14 inches, 12 inches×10 inches, and the like. In the cassette housing unit 21, a plurality of types of electronic cassettes 30 can be housed regardless of the type. The cassette housing unit 21 has a function of charging the battery of the housed electronic cassette 30.

The handle 22 is provided at a position protruding above the central unit 15. The handle 22 has a cylindrical shape that is long in the Y-axis direction (refer to FIG. 5). The handle 22 is gripped by the operator OP (refer to FIG. 4), such as a radiology technician, in order to steer the carriage unit 10.

An irradiation switch 32 is attached to the upper portion of the cassette housing unit 21. The irradiation switch 32 is a switch for the operator OP to give an instruction to start the emission of radiation. An extension cable (not shown) is connected to the irradiation switch 32, so that the irradiation switch 32 can be used by being detached from the central unit 15. The irradiation switch 32 is, for example, a two-stage pressing type switch. The irradiation switch 32 generates a warm-up command signal in a case where the irradiation switch 32 is pressed to the first stage (half-pressed), and generates an irradiation start command signal in a case where the irradiation switch 32 is pressed to the second stage (fully pressed). Although not shown, a battery for supplying power to each unit is built into the central unit 15.

The column unit 16 has a prismatic shape, and is erected along the Z-axis direction. The column unit 16 is disposed at a position above the front wheel 11 and at the center of the carriage unit 10 in the Y-axis direction. A voltage generator 33 is provided in the column unit 16.

The arm unit 17 has a prismatic shape similarly to the column unit 16. The arm unit 17 has a proximal end attached to the column unit 16 and a distal end, which is a free end opposite to the proximal end and to which the irradiation unit 18 is attached.

The irradiation unit 18 is configured to include a radiation tube 40 and an irradiation field limiter 41. The radiation tube 40 generates, for example, X-rays as radiation. A filament, a target, a grid electrode, and the like (all not shown) are provided in the radiation tube 40. A voltage from the voltage generator 33 is applied between the filament serving as a cathode and the target serving as an anode. A voltage applied between the filament and the target is called a tube voltage. The filament emits thermoelectrons according to the applied tube voltage toward the target. The target emits radiation by the impact of thermoelectrons from the filament. The grid electrode is disposed between the filament and the target. The grid electrode changes the flow rate of thermoelectrons from the filament toward the target in accordance with the voltage applied from the voltage generator 33. The flow rate of thermoelectrons from the filament toward the target is called a tube current. The tube voltage and the tube current are set as irradiation conditions together with the irradiation time.

In a case where the irradiation switch 32 is half-pressed to generate a warm-up command signal, the filament is preheated and simultaneously the rotation of the target is started. Warm-up is completed at a point in time at which the filament reaches a specified temperature and the target reaches a specified speed. In a state in which the warm-up is completed, in a case where the irradiation switch 32 is fully pressed to generate an irradiation start command signal, a tube voltage is applied from the voltage generator 33 and radiation is generated from the radiation tube 40. In a case where the irradiation time set in the irradiation conditions has passed from the start of the generation of radiation, the application of the tube voltage is stopped and the emission of the radiation is ended.

The irradiation field limiter 41 limits the irradiation field of the radiation generated from the radiation tube 40. The irradiation field limiter 41 has, for example, a configuration in which four shielding plates, such as lead for shielding radiation, are disposed on the sides of a quadrangle and a quadrangular exit opening that transmits radiation is formed in the central portion. The irradiation field limiter 41 changes the size of the exit opening by changing the position of each shielding plate, thereby changing the irradiation field.

Figure 2:
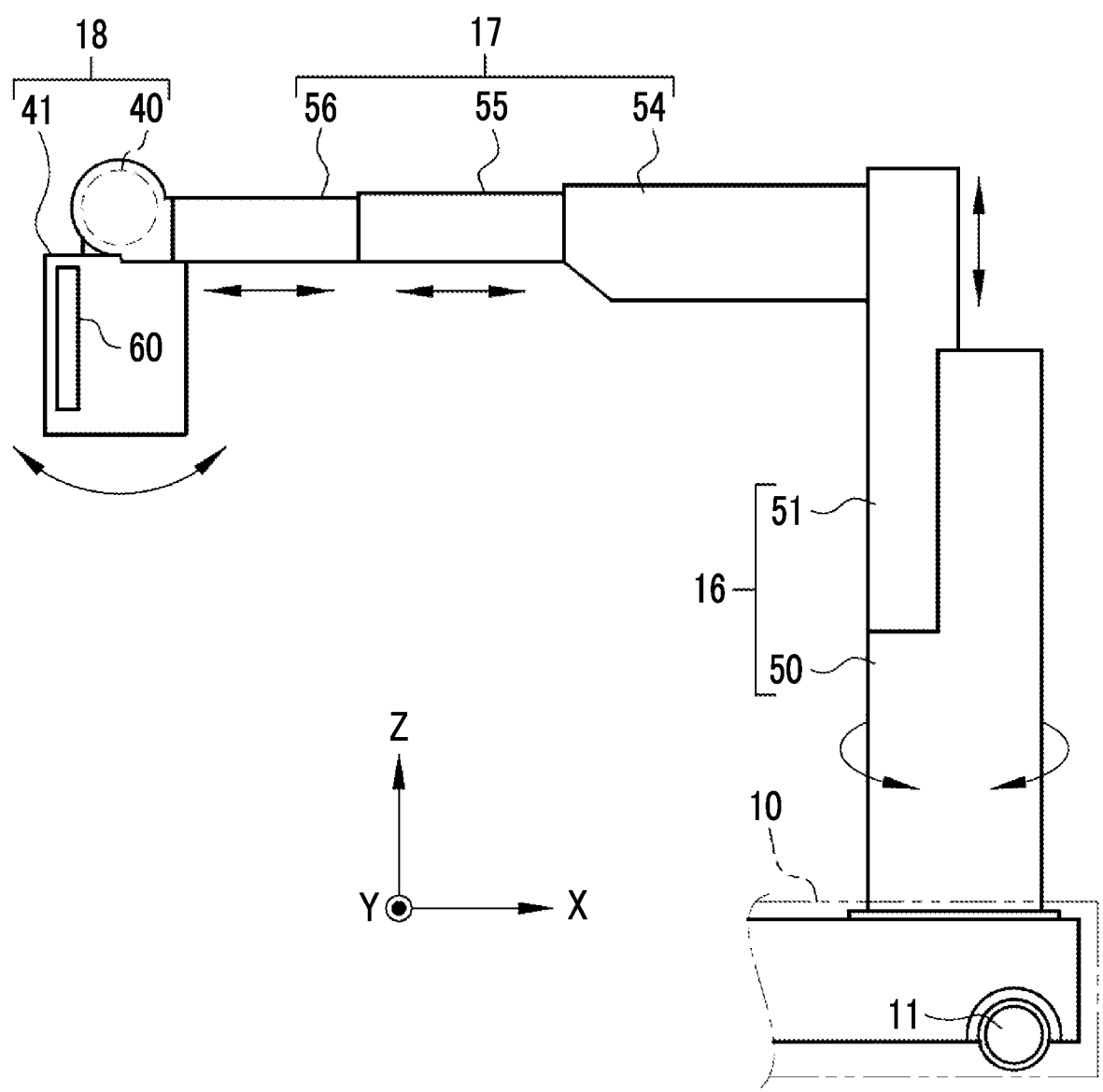
FIG. 2 is a diagram showing the rotation direction and the movement direction of a column unit, the movement direction of an arm unit, and the rotation direction of an irradiation unit.

As shown in FIG. 2, the column unit 16 has a first column 50 and a second column 51. The first column 50 is provided on the upper surface of the carriage unit 10. The first column 50 can rotate around the Z axis with respect to the carriage unit 10. The second column 51 can move up and down along the Z-axis direction with respect to the first column 50.

The arm unit 17 has a fixed arm 54, a first arm 55, and the second arm 56. The fixed arm 54 is bent at a right angle with respect to the second column 51. The proximal end of the fixed arm 54 is attached to the second column 51. The first arm 55 is attached to the distal end of the fixed arm 54. That is, the fixed arm 54 connects the second column 51 and the first arm 55 to each other. The irradiation unit 18 is attached to the distal end of the second arm 56. The first arm 55 can move back and forth with respect to the fixed arm 54 along the bending direction of the fixed arm 54 perpendicular to the Z axis (in FIG. 2, an X-axis direction indicating the front-rear direction of the mobile radiographic imaging apparatus 2). The second arm 56 can move back and forth with respect to the first arm 55 along the bending direction of the fixed arm 54 perpendicular to the Z axis (in FIG. 2, the X-axis direction).

Figure 3:
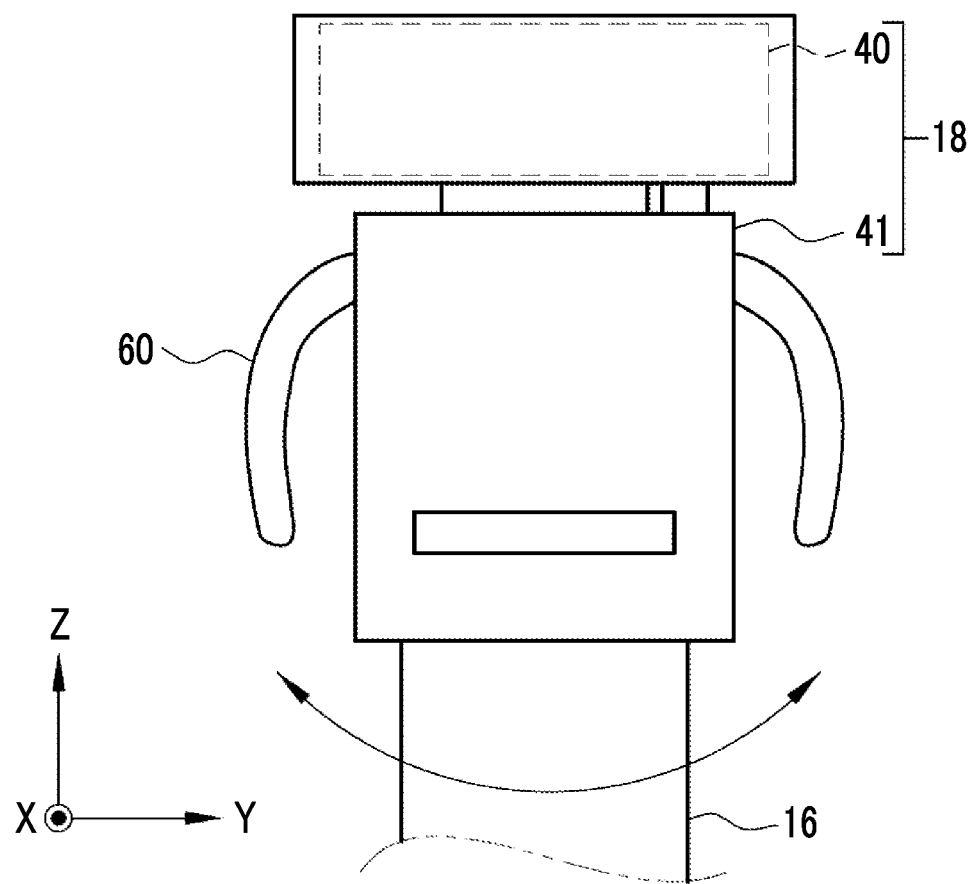
FIG. 3 is a diagram showing the rotation direction of the irradiation unit.

The irradiation unit 18 can rotate around an axis parallel to the width direction (in FIG. 2, the Y axis). As shown in FIG. 3, the irradiation unit 18 can rotate around an axis (in FIG. 2, the X axis) parallel to the front-rear direction.

A handgrip 60 is provided in the irradiation field limiter 41. The handgrip 60 is gripped by the operator OP in the case of moving the second arm 56 back and forth along the bending direction of the fixed arm 54 perpendicular to the Z axis. In addition, the handgrip 60 is gripped by the operator OP in the case of rotating the irradiation unit 18 around an axis parallel to the width direction and in the case of rotating the irradiation unit 18 around an axis parallel to the front-rear direction.

Figure 4:
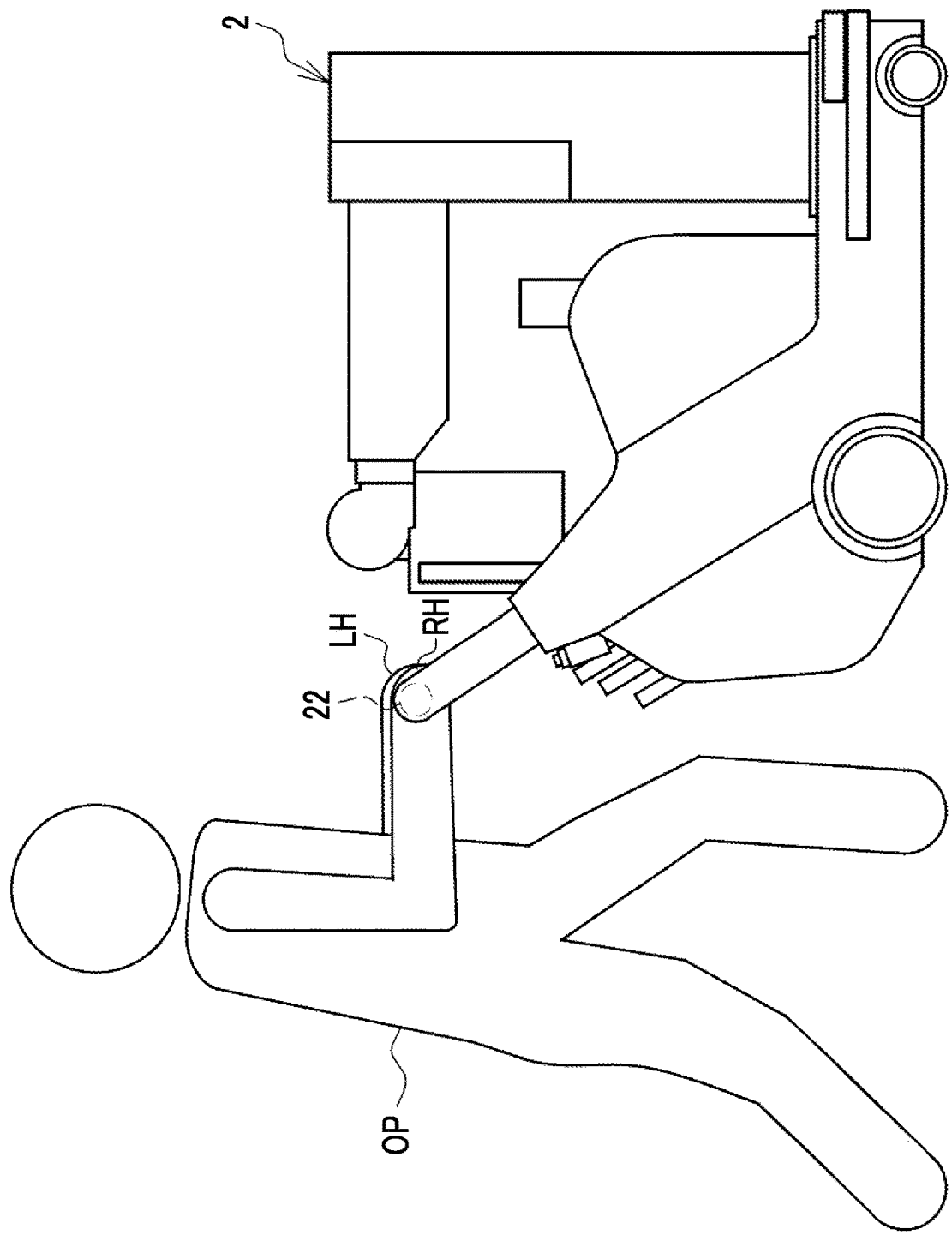
FIG. 4 is a diagram showing the situation of manual travel.

As shown in FIG. 4, the mobile radiographic imaging apparatus 2 is moved in the hospital by manual travel. The manual travel mode is a travel mode in which the carriage unit 10 travels by the operation of the operator OP on the handle 22. The operation of the operator OP on the handle 22 is an operation in which the operator OP grips the handle 22 to change the way in which the force is applied to the handle 22 or adjust the direction in which the force is applied to the handle 22. In manual travel, by operating the handle 22, the operator OP independently determines the travel speed and the travel direction of the carriage unit 10 to cause the carriage unit 10 to travel. FIG. 4 shows a state in which the operator OP is manually traveling while gripping the handle 22 with both a right hand RH and a left hand LH.

The rear wheel driving unit 13 rotationally drives the rear wheel 12 in order to assist the manual travel. However, the driving of the rear wheel driving unit 13 in manual travel is a driving according to the force applied to the carriage unit 10 by the operator OP. For this reason, in a state in which the carriage unit 10 is stationary, the carriage unit 10 naturally does not travel unless the force of the operator OP is applied. On the contrary, the carriage unit 10 does not travel only with the force of the operator OP, and the carriage unit 10 travels only with the assistance of the rear wheel driving unit 13. In addition, the carriage unit 10 may be able to travel only with the force of the operator OP, and the assistance of the rear wheel driving unit 13 may be for reducing the load on the operator OP.

The force applied to the carriage unit 10 by the operator OP is detected using, for example, a piezoelectric sensor, and the rear wheel driving unit 13 is driven according to the detection result. More specifically, a pair of piezoelectric sensors are provided on the left and right. Then, the force applied mainly by the left hand LH of the operator OP and the force applied mainly by the right hand RH of the operator OP are separately detected. In a case where the forces detected by the pair of piezoelectric sensors are the same, the rear wheel driving unit 13 rotates the left and right rear wheels 12 at the same rotation speed so that the carriage unit 10 moves straight. In a case where the force detected by the right piezoelectric sensor is greater than the force detected by the left piezoelectric sensor, the rear wheel driving unit 13 increases the rotation speed of the right rear wheel 12 rather than that of the left rear wheel 12 so that the carriage unit 10 turns to the left. In a case where the force detected by the left piezoelectric sensor is greater than the force detected by the right piezoelectric sensor, the rear wheel driving unit 13 increases the rotation speed of the left rear wheel 12 rather than that of the right rear wheel 12 so that the carriage unit 10 turns to the right.

Figure 5:
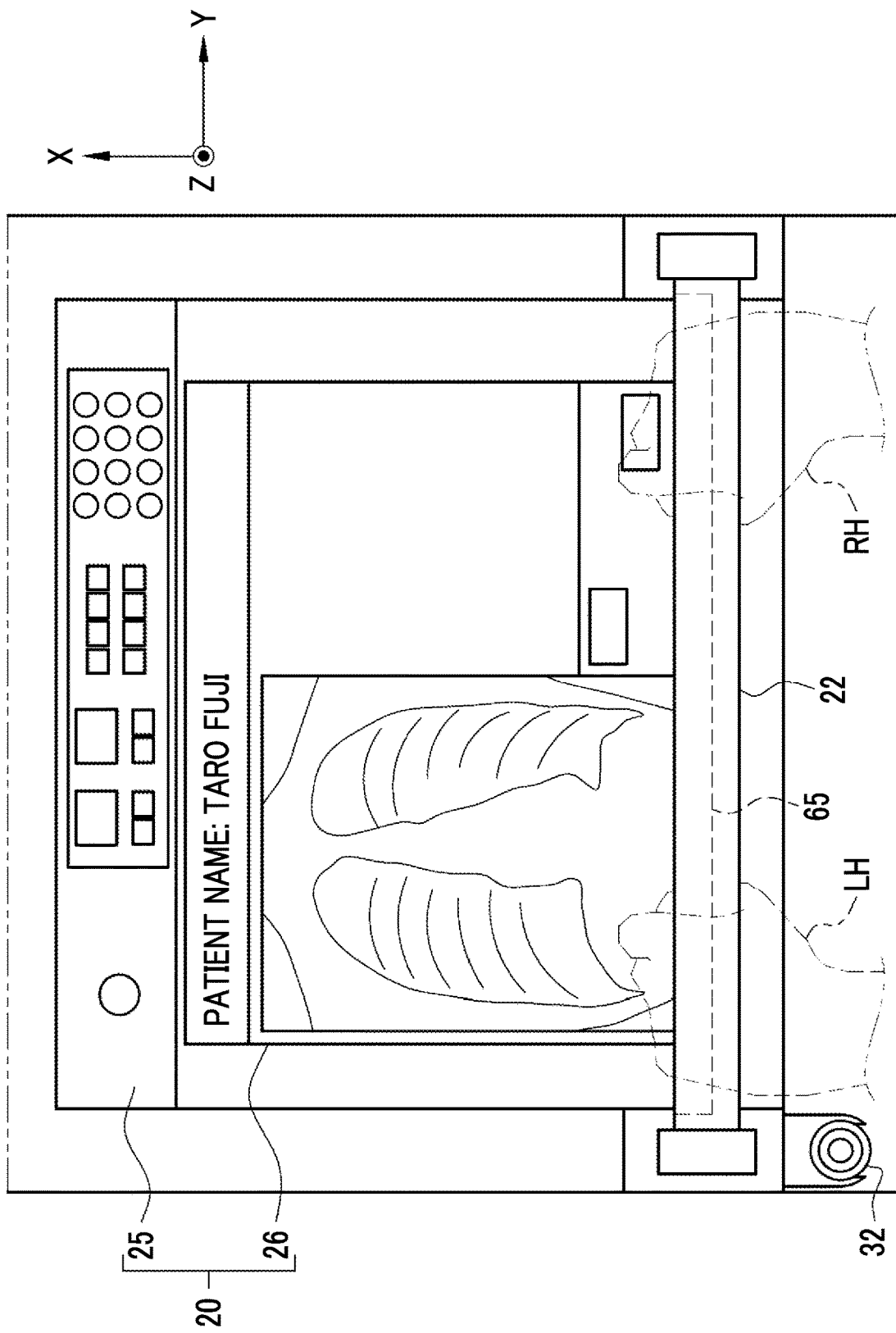
FIG. 5 is a diagram showing a main body unit viewed from the upper surface side.

As shown in FIG. 5, a lock release switch 65 for releasing the rotation lock of the rear wheel 12 by the rear wheel driving unit 13 is provided in the whole front portion of the handle 22. The lock release switch 65 detects that the operator OP has gripped the handle 22. More specifically, the lock release switch 65 detects the contact of the hand of the operator OP with the handle 22. The lock release switch 65 is, for example, a sensor that detects a hand contact based on the capacitance change or a sensor that detects a hand contact based on the temperature change. Alternatively, the lock release switch 65 may be a mechanical lever switch that protrudes from the surface of the handle 22 and is turned off in a case where the handle 22 is not gripped by hand and is retracted into the handle 22 and is turned on in a case where the handle 22 is gripped by hand. In FIG. 5, the broken line indicates a state in which the handle 22 is gripped by both a right hand RH and a left hand LH of the operator OP.

Figure 6:
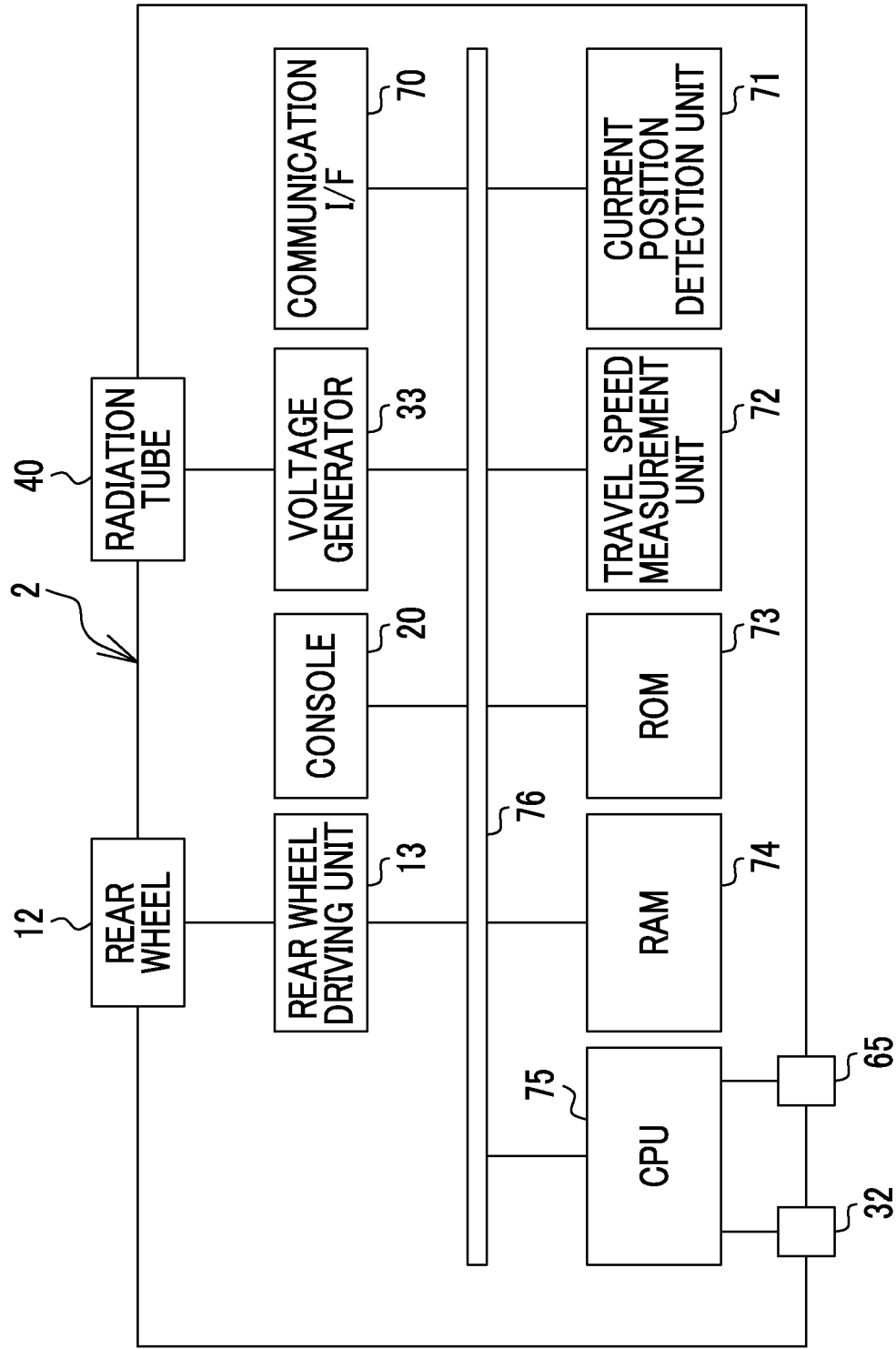
FIG. 6 is a block diagram of the mobile radiographic imaging apparatus.

In FIG. 6, the mobile radiographic imaging apparatus 2 has a communication interface (I/F) 70, a current position detection unit 71, a travel speed measurement unit 72, a read only memory (ROM) 73, a random access memory (RAM) 74, and a central processing unit (CPU) 75 in addition to the rear wheel driving unit 13, the console 20, and the voltage generator 33 described above. The rear wheel driving unit 13, the console 20, the voltage generator 33, the communication IF 70, the ROM 73, the RAM 74, and the CPU 75 are connected to each other through a bus line 76. The ROM 73, the RAM 74, the CPU 75, and the bus line 76 are examples of a "computer" according to the technique of the present disclosure.

The communication I/F 70 includes a wireless communication interface for wireless communication with the electronic cassette 30. In addition, the communication I/F 70 includes a network interface for communicating with an external apparatus other than the electronic cassette 30 through a network. As an example of the external apparatus, there is a radiology information system (RIS) that manages information regarding radiographic imaging, such as imaging schedule information 96 (refer to FIGS. 8 and 10) indicating the schedule of radiographic imaging. Examples of the network include the Internet or a wide area network (WAN), such as a public communication network.

The current position detection unit 71 detects the current position of the carriage unit 10 on the floor on which the carriage unit 10 manually travels. The current position of the carriage unit 10 refers to, for example, a position 1 m ahead of the front wheel 11. Hereinafter, the current position of the carriage unit 10 is simply referred to as a "current position".

Figure 8:
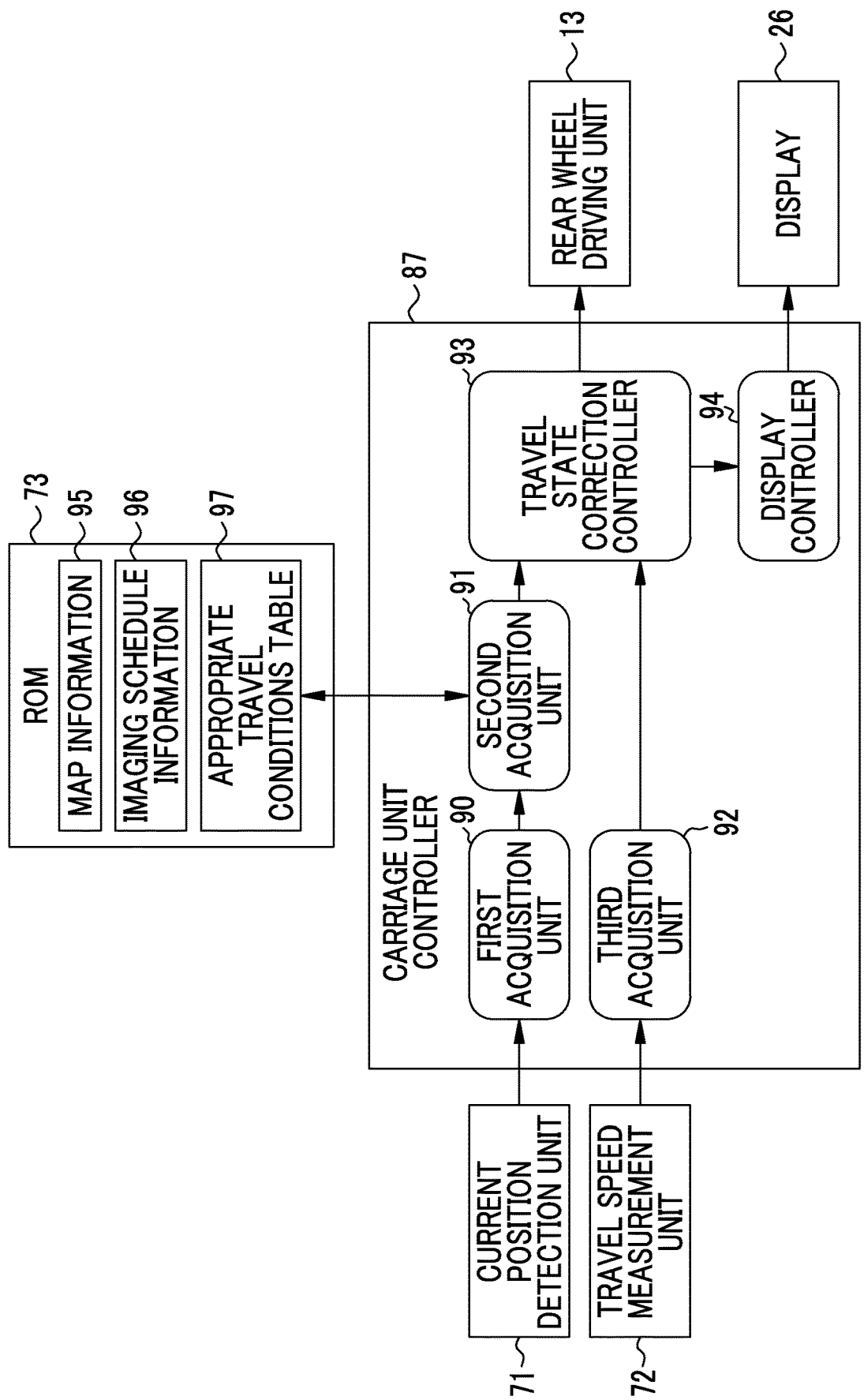
FIG. 8 is a block diagram showing a carriage unit controller.
Figure 9:
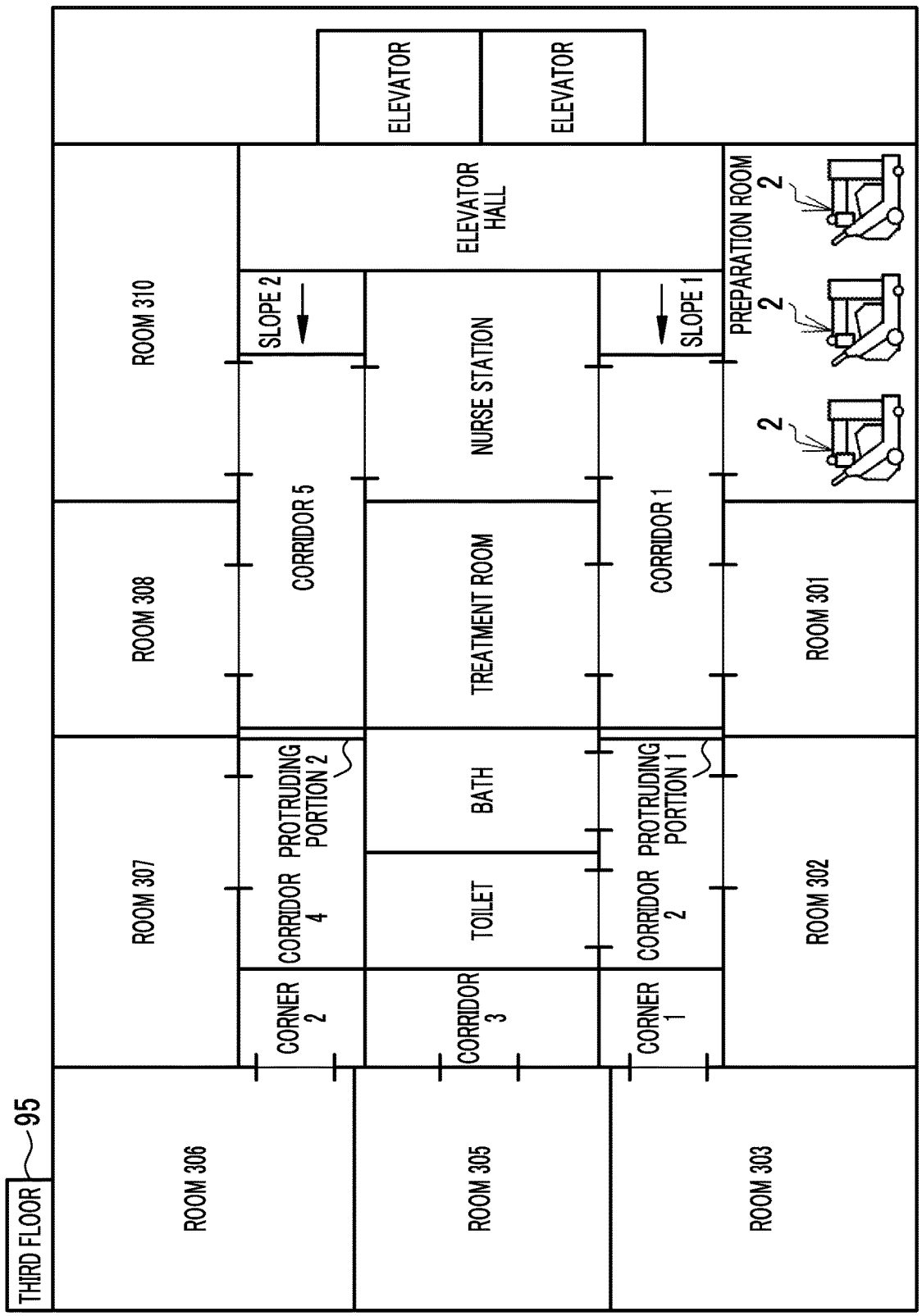
FIG. 9 is a diagram showing an example of map information.

As a specific example of the current position detection unit 71, the following example can be considered. That is, the current position detection unit 71 includes sensors that detect the travel distance and the travel direction of the carriage unit 10, such as a rotary encoder that detects the rotation amount of the rear wheel 12, a gyro sensor, and an acceleration sensor. Then, the current position is detected by comparing the position of the carriage unit 10 derived from the travel distance and the travel direction detected by such sensors with map information 95 (FIGS. 8 and 9).

The travel distance and the travel direction of the carriage unit 10 are the travel distance and the travel direction with respect to the reference position on the floor. The reference position is designated, for example, by displaying the map of the floor on the display 26 and causing the operator OP to perform designation through the map of the floor.

In addition, the following configuration may be adopted. That is, markers that are different for each position are disposed at a plurality of positions on the floor. A camera is mounted in the mobile radiographic imaging apparatus 2, and each marker is imaged by the camera so that the marker is image-recognized by an image recognition unit. Then, the position indicated by the image-recognized marker is detected as the current position of the carriage unit 10 on the floor. The current position detection unit 71 in this case includes a camera for imaging the marker and an image recognition unit for performing image recognition of the marker. In addition to the methods described above, a configuration in which a magnetic material is embedded in the corridor and a magnetic field generated by the magnetic material is detected by a magnetic sensor or a configuration using a distance ranging sensor, such as laser imaging detection and ranging (LIDAR), may be adopted.

The travel speed measurement unit 72 measures the travel speed of the carriage unit 10 in manual travel. Hereinafter, the travel speed of the carriage unit 10 measured by the travel speed measurement unit 72 will be referred to as a first measurement value.

The travel speed measurement unit 72 has a configuration using the principle of a speedometer of an automobile or the like, for example. More specifically, the travel speed measurement unit 72 includes a rotary encoder that detects the rotation amount of the rear wheel 12 and a conversion unit that converts the rotation amount detected by the rotary encoder into a first measurement value using a conversion expression prepared in advance.

The ROM 73 stores various programs and various kinds of data added to the various programs. The RAM 74 is a work memory for the CPU 75 to execute processing. The CPU 75 reads a program stored in the ROM 73 to the RAM 74 and executes processing according to the read program. Therefore, the CPU 75 performs overall control of the operation of each unit of the mobile radiographic imaging apparatus 2.

The irradiation switch 32 and the lock release switch 65 are connected to the CPU 75. The irradiation switch 32 outputs a warm-up command signal and an irradiation start command signal to the CPU 75. The lock release switch 65 outputs a detection signal, which indicates that the contact of the hand of the operator OP has been detected, to the CPU 75.

Figure 7:
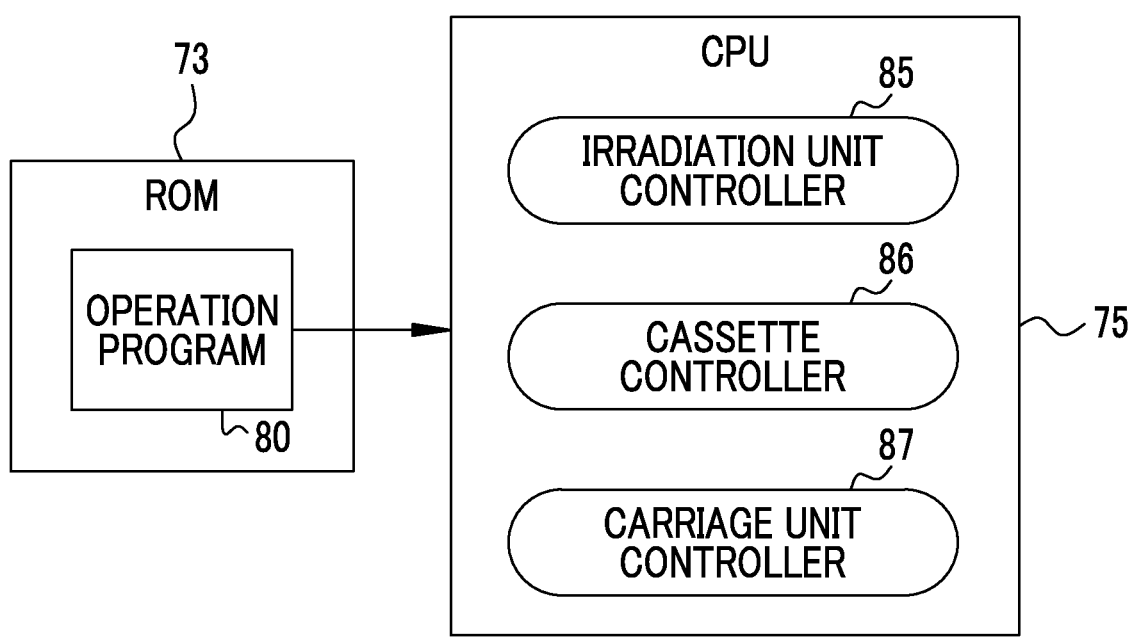
FIG. 7 is a block diagram showing a controller of a CPU of the mobile radiographic imaging apparatus.

In FIG. 7, an operation program 80 is stored in the ROM 73. The operation program 80 is an example of an "operation program of a mobile radiographic imaging apparatus" according to the technique of the present disclosure. The CPU 75 executes the operation program 80 to function as an irradiation unit controller 85, a cassette controller 86, and a carriage unit controller 87 in cooperation with the RAM 74 and the like.

The irradiation unit controller 85 is a controller relevant to the irradiation unit 18. The irradiation unit controller 85 receives irradiation conditions input through the operation console 25, and sets the received irradiation conditions in the voltage generator 33. In addition, the irradiation unit controller 85 receives a warm-up command signal from the irradiation switch 32 and causes the radiation tube 40 to warm up. In addition, the irradiation unit controller 85 receives an irradiation start command signal from irradiation switch 32, and controls the operation of the voltage generator 33 to emit radiation from the radiation tube 40 under the set irradiation conditions.

The cassette controller 86 is a controller relevant to the electronic cassette 30. The cassette controller 86 controls the operation of the electronic cassette 30 by transmitting various control signals to the electronic cassette 30 through the communication I/F 70. The control signal transmitted to the electronic cassette 30 is, for example, a signal for giving an instruction for the accumulation of charges according to radiation in accordance with the irradiation start timing and a signal for reading the accumulated charges in accordance with the irradiation end timing. The cassette controller 86 receives a radiographic image from the electronic cassette 30 through the communication I/F 70. The cassette controller 86 performs control to display the acquired radiographic image on the display 26.

The carriage unit controller 87 is a controller relevant to the carriage unit 10. The carriage unit controller 87 includes a driving unit controller that controls the driving of the rear wheel driving unit 13. The driving unit controller receives a detection signal from the lock release switch 65, and release the rotation lock of the rear wheel 12 by the rear wheel driving unit 13. In addition, the driving unit controller drives the rear wheel driving unit 13 according to the force that is detected by a piezoelectric sensor or the like and is applied to the carriage unit 10 by the operator OP.

Figure 18:
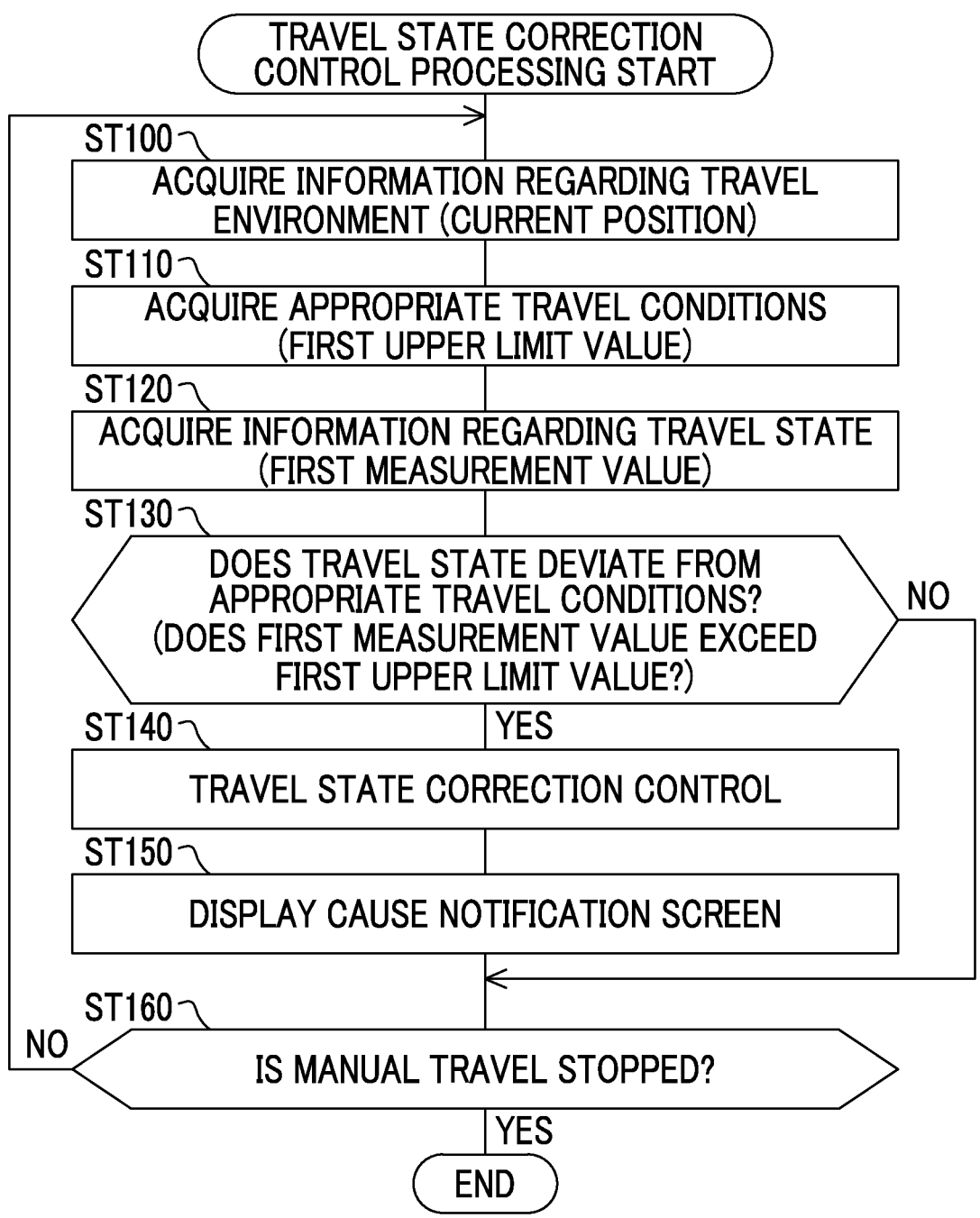
FIG. 18 is a flowchart showing the procedure of travel state correction control processing.

The carriage unit controller 87 executes travel state correction control processing (refer to FIG. 18). In order to execute the travel state correction control processing, as shown in FIG. 8, the carriage unit controller 87 has a first acquisition unit 90, a second acquisition unit 91, a third acquisition unit 92, a travel state correction controller 93, and a display controller 94.

The first acquisition unit 90 acquires information regarding the travel environment of the carriage unit 10. In the present embodiment, the first acquisition unit 90 acquires a current position from the current position detection unit 71 as the information regarding the travel environment. The first acquisition unit 90 outputs the acquired current position to the second acquisition unit 91.

The second acquisition unit 91 acquires appropriate travel conditions of the carriage unit 10 according to the information regarding the travel environment acquired by the first acquisition unit 90 (current position in the present embodiment). The second acquisition unit 91 outputs the acquired appropriate travel conditions to the travel state correction controller 93.

The third acquisition unit 92 acquires information regarding the travel state of the carriage unit 10 in manual travel. In the present embodiment, the third acquisition unit 92 acquires a first measurement value from the travel speed measurement unit 72 as the information regarding the travel state. The third acquisition unit 92 outputs the acquired first measurement value to the travel state correction controller 93.

The travel state correction controller 93 performs travel state correction control. The travel state correction control is a control to make a correction to a travel state satisfying the appropriate travel conditions by controlling the rear wheel driving unit 13 in a case where the travel state (first measurement value in the present embodiment) acquired by the third acquisition unit 92 deviates from the appropriate travel conditions acquired by the second acquisition unit 91. The travel state correction controller 93 outputs the cause to the display controller 94 in a case where the travel state correction control is being performed.

The display controller 94 performs control to display a cause notification screen 100 (refer to FIGS. 17A and 17B) for providing notification of the cause of the travel state correction control from the travel state correction controller 93 on the display 26.

The map information 95, the imaging schedule information 96, and an appropriate travel conditions table 97 are stored in the ROM 73.

As shown in FIG. 9, the map information 95 is information indicating the arrangement of patient rooms and the like on the floor on which the carriage unit 10 manually travels. FIG. 9 shows the map information 95 on the third floor as an example. There are a total of eight patient rooms of room 301, room 302, room 303, room 305, room 306, room 307, room 308, and room 310. In addition to these rooms, there are a preparation room, a treatment room, a nurse station, and the like.

The preparation room is a room where the mobile radiographic imaging apparatus 2 stands by. In the preparation room, the operator OP downloads the imaging schedule information 96 from the RIS and stores the imaging schedule information 96 in the ROM 73, or houses the electronic cassette 30 to be used in the cassette housing unit 21.

With a preparation room as a departure point and a last arrival point, the carriage unit 10 manually travels through respective positions on the third floor, such as an elevator hall, slope 1, slope 2, corridor 1, corridor 2, corridor 3, corridor 4, corridor 5, protruding portion 1, protruding portion 2, corner 1, and corner 2. The elevator hall, slopes 1 and 2, corridors 1 to 5, protruding portions 1 and 2, and corners 1 and 2 are examples of a "travel passage" according to the technique of the present disclosure.

The elevator hall is a portion interposed between two elevators and a nurse station. The slope 1 is a portion inclined downward from the elevator hall to the corridor 1. The slope 2 is a portion inclined downward from the elevator hall to the corridor 5. The corridors 1 and 2 are passages connecting the preparation room, the room 301, and the room 302 to each other. The corridors 4 and 5 are portions connecting the room 307, the room 308, and the room 309 to each other. The corridor 3 is a portion in front of the room 305. The corridor 3 is perpendicular to the corridors 1, 2, 4, and 5. The corridor 3 has a width narrower than the corridors 1, 2, 4, and 5.

The protruding portion 1 is a raised portion that is present at the boundary between the room 301 and the room 302 and has, for example, a height of about 2 to 5 cm and a length of about 2 to 5 cm. The protruding portion 2 is a raised portion that is present at the boundary between the room 307 and the room 308 and has, for example, a height of about 2 to 5 cm and a length of about 2 to 5 cm. The corner 1 is a portion that connects the corridor 2 and the corridor 3 perpendicular to each other and is bent at 900 in front of the room 303. The corner 2 is a portion that connects the corridor 3 and the corridor 4 perpendicular to each other and is bent at 90° in front of the room 306. Coordinates indicating the positions of each room and each portion on the floor are stored in the map information 95.

In FIG. 10, information, such as patient identification data (ID), a patient name, a patient room, and an imaging part, is registered in the imaging schedule information 96. Here, the imaging schedule information 96 for the third floor on Nov. 13, 2018 is shown. Patient rooms for patients for whom radiographic imaging is scheduled are room 302, room 305, and room 307. In addition to these, information, such as patient's age, sex, disease name, and a bed position in the patient room, may be registered.

The imaging schedule information 96 is displayed on the display 26 in response to a request from the operator OP. The operator OP views the imaging schedule information 96 displayed on the display 26 and determines a route along which the carriage unit 10 travels. In a case where the imaging schedule information 96 is the content shown in FIG. 10, the operator OP determines a route along which the carriage unit 10 moves in order from the room 302 to the room 305 and further to the room 307 with the preparation room as a departure point and a last arrival point. The carriage unit controller 87 may create a route based on the imaging schedule information 96.

In FIG. 11, the appropriate travel conditions table 97 is a table in which appropriate travel conditions are registered in association with each of a plurality of positions set in advance on the floor on which the carriage unit 10 manually travels. That is, the ROM 73 in which the appropriate travel conditions table 97 is stored is an example of a "storage unit" according to the technique of the present disclosure.

In FIG. 11, as a plurality of positions set in advance on the floor on which the carriage unit 10 manually travels, each portion on the third floor described above, that is, the elevator hall, slopes 1 and 2, corridors 1 to 5, protruding portions 1 and 2, and corners 1 and 2 are shown. Then, a first upper limit value of the travel speed of the carriage unit 10 is registered as the appropriate travel conditions. More specifically, 1.0 km/h is registered for the elevator hall, 1.5 km/h is registered for the slopes 1 and 2 (in the case of a downhill), and 3.0 km/h is registered for the corridors 1, 2, 4, and 5. In addition, 1.5 km/h is registered for the protruding portions 1 and 2, 1.0 km/h is registered for the corners 1 and 2, and 1.5 km/h is registered for the corridor 3. The first upper limit value is registered by the representative of the operator OP, for example. Alternatively, the first upper limit value may be registered based on the first measurement value in a case where the representative of the operator OP actually performs manual travel. Instead of or in addition to the protruding portion, a recessed portion may be registered as a position. Alternatively, a portion where a protruding portion and a recessed portion are connected to each other may be registered as a position.

There are many people in the elevator hall. Each person is an obstacle that is present in the travel passage and can be an obstacle to manual travel. For this reason, in other words, there are many obstacles in the elevator hall that can be obstacles to manual travel. Therefore, for the elevator hall, a relatively slow 1.0 km/h is set as the first upper limit value. The first upper limit value of the elevator hall is an example of a "first upper limit value according to the number of obstacles that can be obstacles to manual travel" according to the technique of the present disclosure.

On the slopes 1 and 2, the carriage unit 10 is accelerated in the case of a downhill. Therefore, for the slopes 1 and 2, a relatively slow 1.5 km/h is set as the first upper limit value. The first upper limit value of the slopes 1 and 2 is an example of a "first upper limit value according to the inclination state of the travel passage" according to the technique of the present disclosure. The case where the slope 1 is a downhill is a case where the carriage unit 10 is made to travel toward the corridor 1 from the elevator hall. The case where the slope 2 is a downhill is a case where the carriage unit 10 is made to travel toward the corridor 5 from the elevator hall.

The corridors 1, 2, 4, and 5 have widths narrower than the corridor 3. Therefore, for the corridors 1, 2, 4, and 5, a relatively fast 3.0 km/h is set as the first upper limit value. On the other hand, for the corridor 3, a relatively slow 1.5 km/h is set as the first upper limit value. The first upper limit values of the corridors 1 to 5 are examples of a "first upper limit value according to the width of the travel passage" according to the technique of the present disclosure.

In the protruding portions 1 and 2, an impact is applied to the carriage unit 10. Therefore, for the protruding portions 1 and 2, a relatively slow 1.5 km/h is set as the first upper limit value. The first upper limit value of the protruding portions 1 and 2 is an example of a "first upper limit value according to the unevenness state of the travel passage" according to the technique of the present disclosure.

The corners 1 and 2 have poor visibility. Therefore, for the corners 1 and 2, a relatively slow 1.0 km/h is set as the first upper limit value. The first upper limit value of the corners 1 and 2 is an example of a "first upper limit value according to whether or not the travel passage is a corner" according to the technique of the present disclosure.

In FIG. 11, in order to help understanding, the cause of setting the first upper limit value of each position is shown beside the appropriate travel conditions table 97. This setting cause is the cause of performing travel state correction control, which is notified by the display controller 94.

Figure 12:
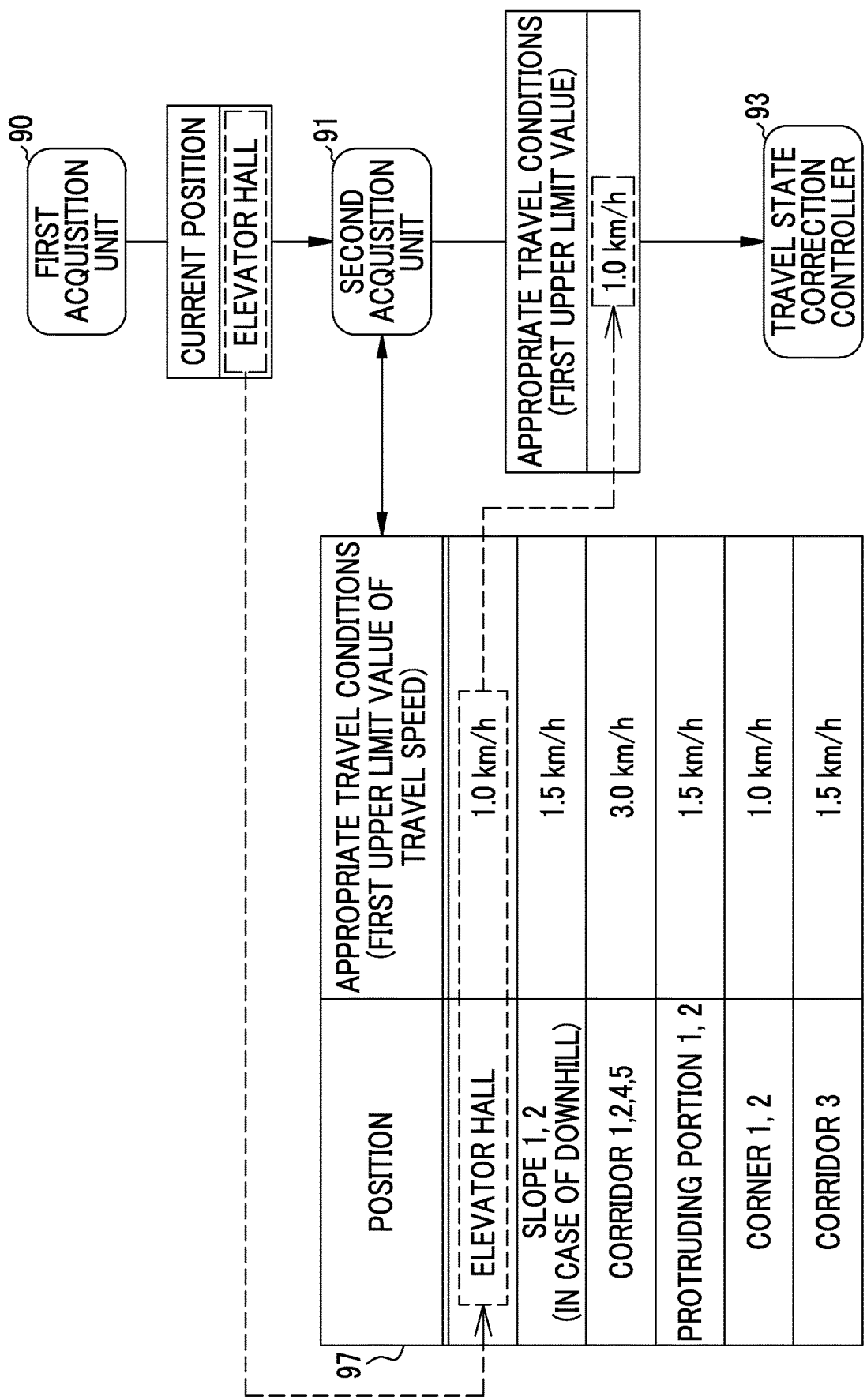
FIG. 12 is a diagram showing the outline of processing of a second acquisition unit.

In FIG. 12, the second acquisition unit 91 reads and acquires appropriate travel conditions (first upper limit value in the present embodiment), which correspond to the current position acquired by the first acquisition unit 90, from the appropriate travel conditions table 97 in the ROM 73. FIG. 12 illustrates a case where the current position acquired by the first acquisition unit 90 is an elevator hall. In this case, the second acquisition unit 91 reads and acquires the first upper limit value of 1.0 km/h, which is the appropriate travel conditions corresponding to the elevator hall, from the appropriate travel conditions table 97.

A case where the current position is a position 1 m ahead of the front wheel 11 as described above is considered. In this case, the timing at which the second acquisition unit 91 acquires the appropriate travel conditions is a timing at which the carriage unit 10 reaches 1 m ahead of a position where the carriage unit 10 is present. For this reason, in a case where the position ahead of the carriage unit 10 is, for example, the protruding portions 1 and 2, 1.5 km/h that is the first upper limit value of the protruding portions 1 and 2 is acquired by the second acquisition unit 91 at a time at which the carriage unit 10 reaches 1 m ahead of the protruding portions 1 and 2.

Figure 13:
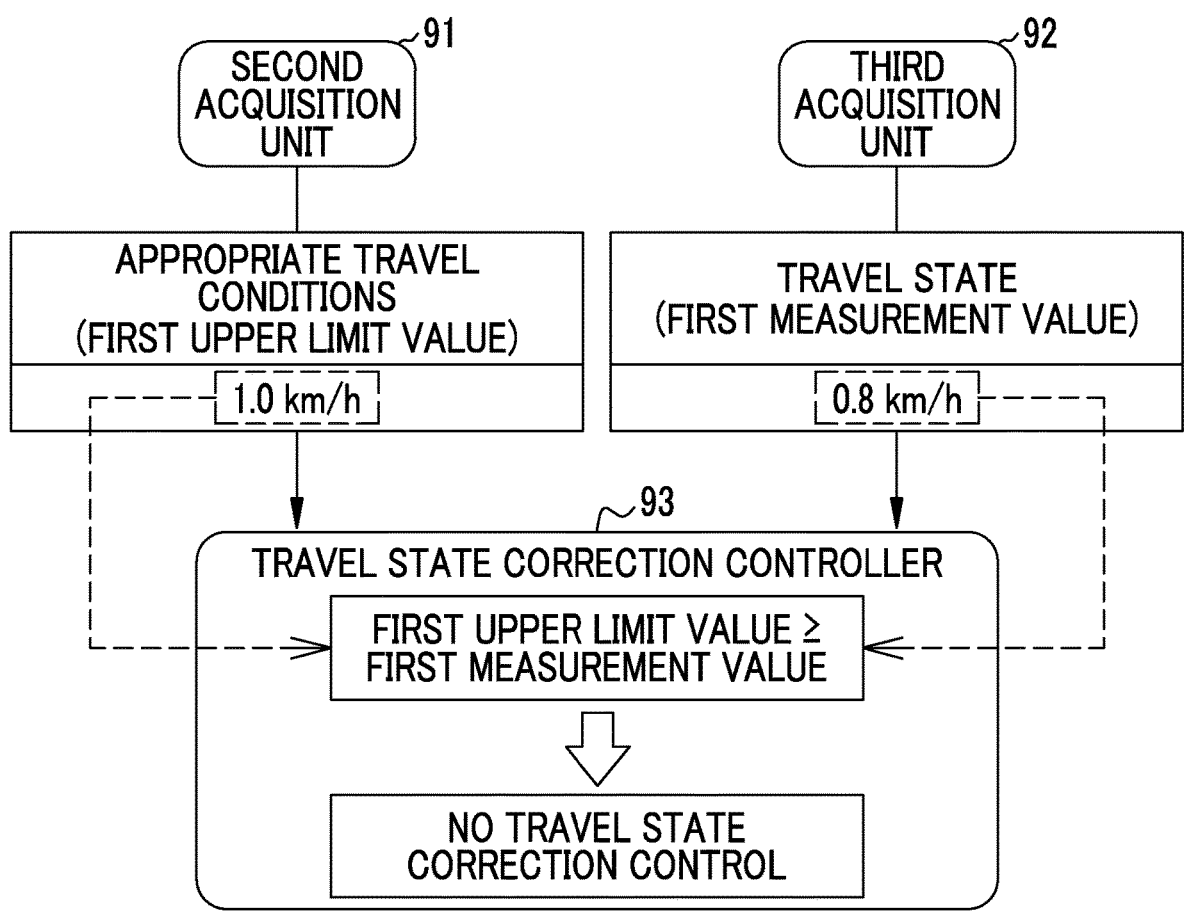
FIG. 13 is a diagram showing the outline of processing of a travel state correction controller.

As shown in FIG. 13, in a case where the travel state acquired by the third acquisition unit 92 does not deviate from the appropriate travel conditions acquired by the second acquisition unit 91, the travel state correction controller 93 does not perform travel state correction control. In the present embodiment, the appropriate travel conditions are the first upper limit value, and the travel state is the first measurement value. For this reason, in other words, the travel state correction controller 93 does not perform travel state correction control in a case where the first measurement value acquired by the third acquisition unit 92 is equal to or less than the first upper limit value acquired by the second acquisition unit 91 (first upper limit value≥first measurement value).

FIG. 13 illustrates a case where the first upper limit value from the second acquisition unit 91 is 1.0 km/h and the first measurement value from the third acquisition unit 92 is 0.8 km/h. In this case, since the first measurement value is equal to or less than the first upper limit value, the travel state correction controller 93 does not perform travel state correction control.

Figure 14:
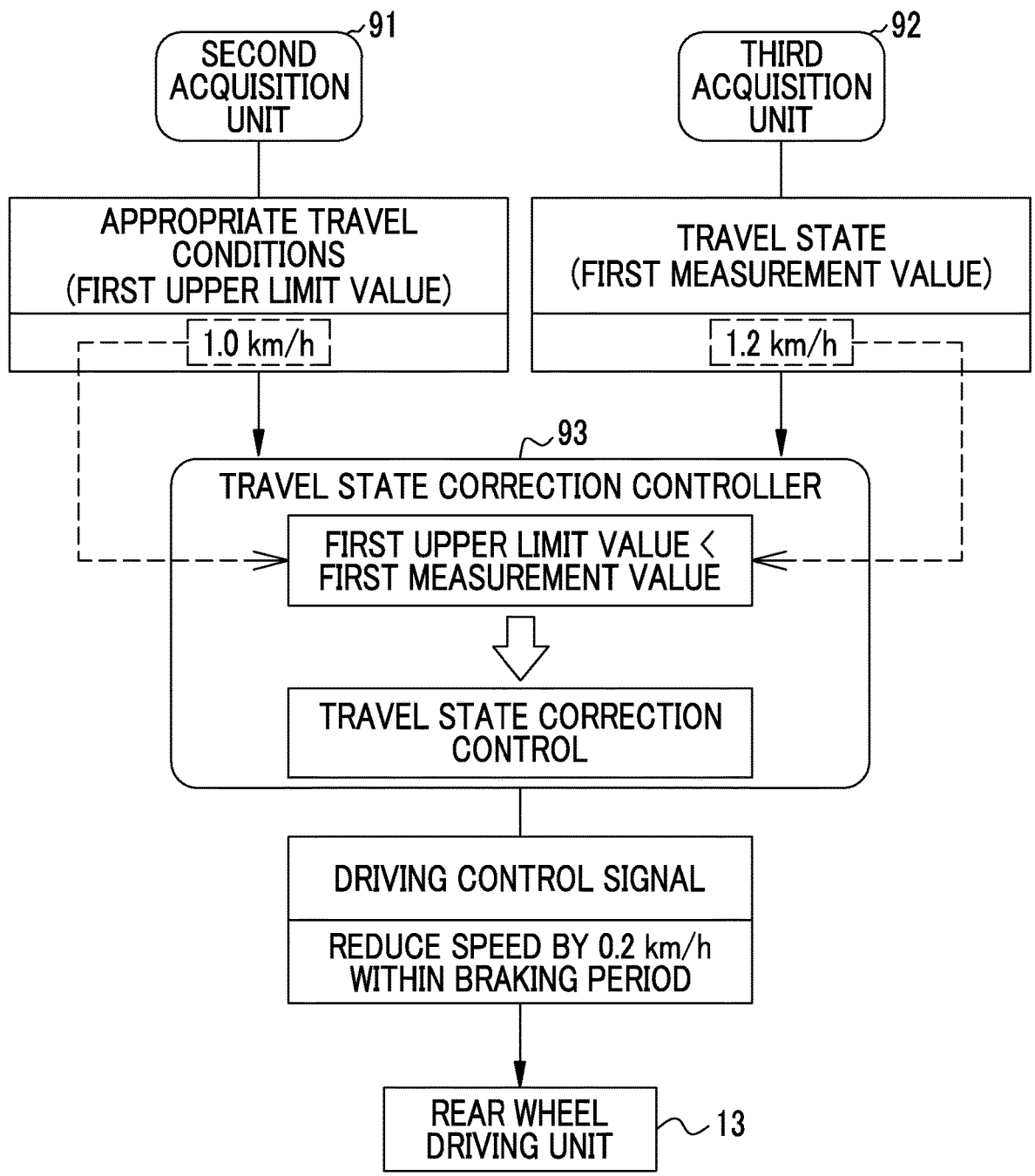
FIG. 14 is a diagram showing the outline of processing of the travel state correction controller.

On the other hand, as shown in FIG. 14, in a case where the travel state acquired by the third acquisition unit 92 deviates from the appropriate travel conditions acquired by the second acquisition unit 91, the travel state correction controller 93 performs travel state correction control. In other words, the travel state correction controller 93 performs travel state correction control in a case where the first measurement value acquired by the third acquisition unit 92 exceeds the first upper limit value acquired by the second acquisition unit 91 (first upper limit value<first measurement value). As the travel state correction control, the travel state correction controller 93 outputs a driving control signal, which is for reducing the speed of the carriage unit 10 by the difference between the first upper limit value and the first measurement value within a braking period set in advance, to the rear wheel driving unit 13. The braking period is in units of several seconds, for example, three seconds.

Specifically, the driving control signal for reducing the speed of the carriage unit 10 is a signal for applying a load in a backward direction to the rear wheel 12. For example, the load in the backward direction is generated by applying a brake to the rear wheel 12. Alternatively, the load in the backward direction is generated by applying a torque in the backward direction to the rear wheel 12. The load in the backward direction is naturally smaller than the force applied to the carriage unit 10 by the operator OP.

Figure 15:
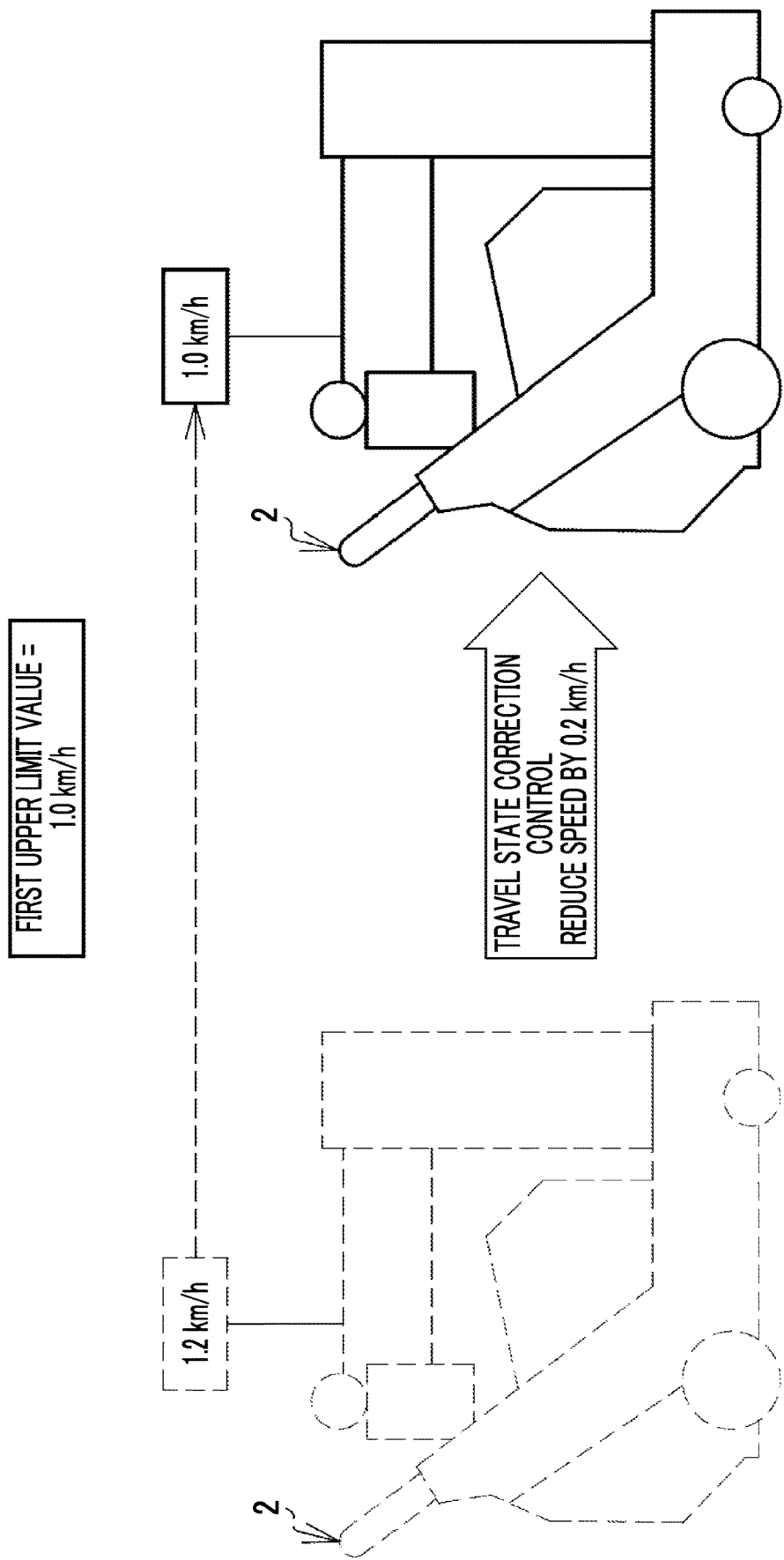
FIG. 15 is a diagram showing how the travel speed of a carriage unit is reduced by travel state correction control.

FIG. 14 illustrates a case where the first upper limit value from the second acquisition unit 91 is 1.0 km/h as in FIG. 13 and the first measurement value from the third acquisition unit 92 is 1.2 km/h. In this case, since the first measurement value exceeds the first upper limit value, the travel state correction controller 93 performs travel state correction control. Since the difference between the first upper limit value and the first measurement value is 0.2 km/h, the travel state correction controller 93 outputs a driving control signal for reducing the speed of the carriage unit 10 by 0.2 km/h within the braking period. By performing such travel state correction control, as shown in FIG. 15, the travel speed of the mobile radiographic imaging apparatus 2 is reduced from 1.2 km/h to 1.0 km/h.

Figure 16:
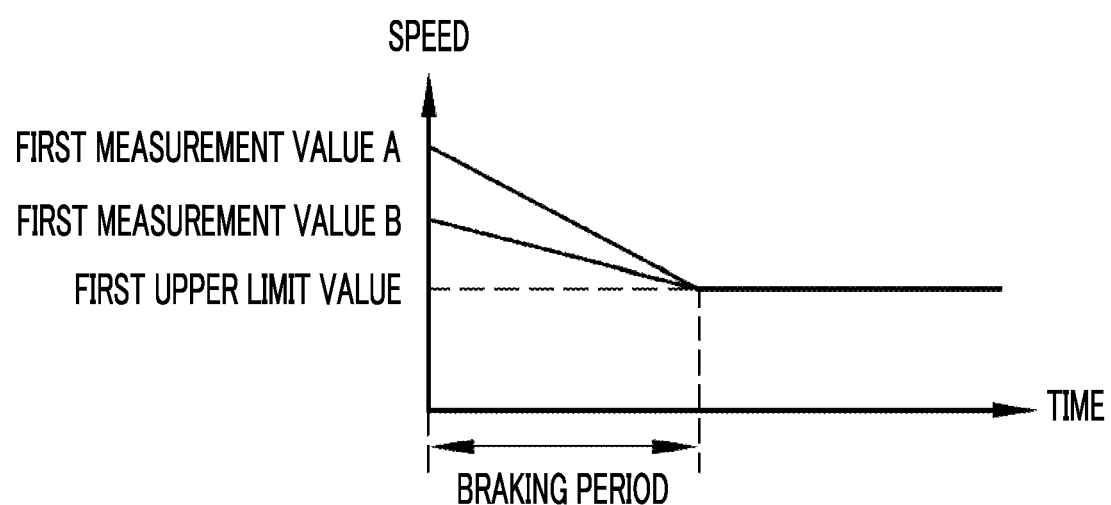
FIG. 16 is a graph showing that the travel speed of the carriage unit is reduced within a braking period by travel state correction control.

As shown in FIG. 16, in a case where the difference from the first upper limit value is relatively large as in the case of a first measurement value A, the load on the rear wheel 12 by the travel state correction control is relatively large in order to change the speed to the first upper limit value within the braking period. On the other hand, in a case where the difference from the first upper limit value is relatively small as in the case of a first measurement value B, the load on the rear wheel 12 by the travel state correction control is smaller than that in the case of the first measurement value A. As described above, the travel state correction controller 93 changes the way of applying the load to the rear wheel 12 according to the difference between the first upper limit value and the first measurement value. In addition, the braking period may be changed according to the difference between the first upper limit value and the first measurement value, such as increasing the braking period as the difference between the first upper limit value and the first measurement value increases.

Figure 17A:
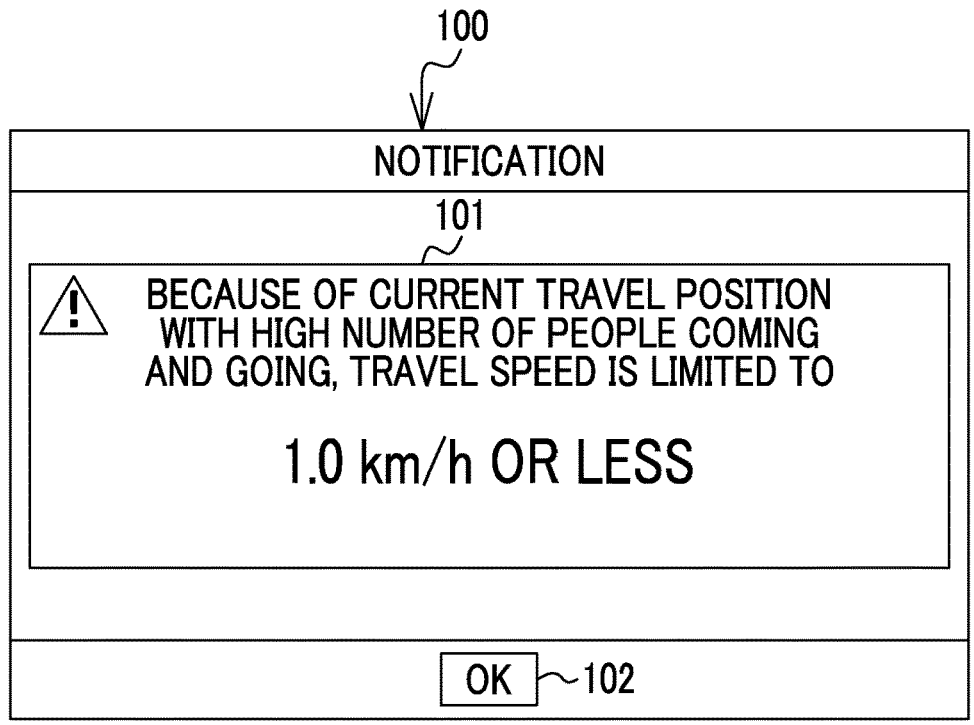
FIGS. 17A and 17B are diagrams showing a cause notification screen, where
Figure 17B:
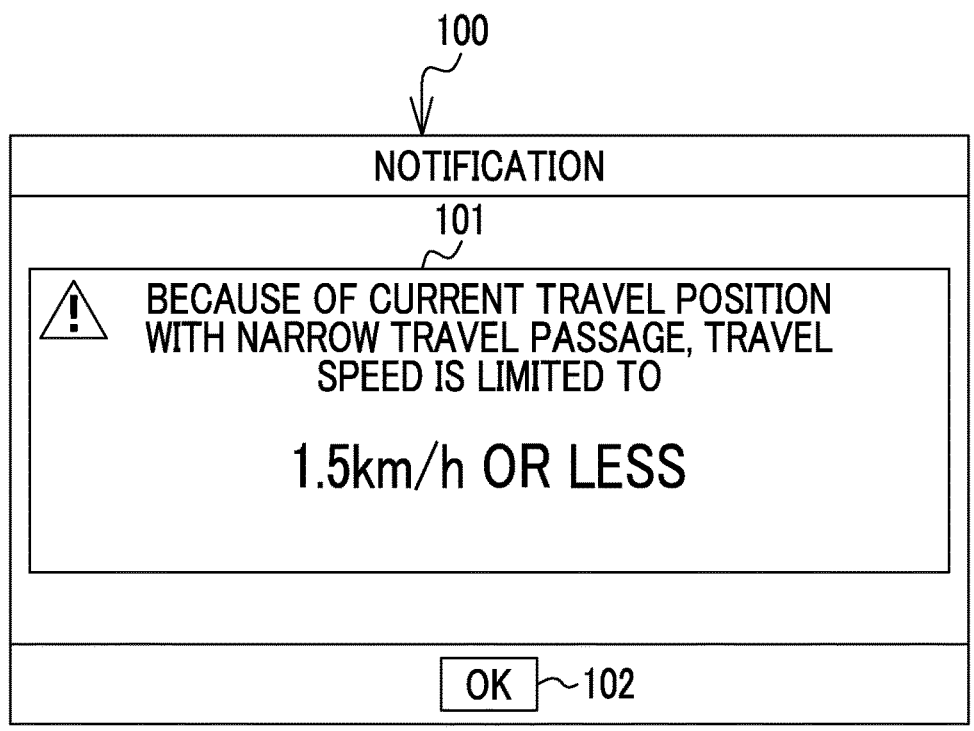

In FIGS. 17A and 17B, a message 101 and an OK button 102 are displayed on the cause notification screen 100. The message 101 is a sentence indicating the cause of performing travel state correction control and the content of travel state correction control. The OK button 102 is a button for deleting the display of the cause notification screen 100.

FIG. 17A illustrates the cause notification screen 100 in a case where the current position is an elevator hall where the number of people coming and going is high. In this case, the message 101 is the content indicating that the cause of the travel state correction control is "the number of obstacles" and the travel speed is limited to the first upper limit value of 1.0 km/h or less. FIG. 17B illustrates the cause notification screen 100 in a case where the current position is the corridor 3 that is a position where the width of the travel passage is narrow. In this case, the message 101 is the content indicating that the cause of the travel state correction control is the "width of travel passage" and the travel speed is limited to the first upper limit value of 1.5 km/h or less.

Next, the operation based on the above configuration will be described with reference to the flowchart shown in FIG. 18. In FIG. 18, travel state correction control processing will be described. The travel state correction control processing is processing executed by the CPU 75 in accordance with the operation program 80. The CPU 75 executes the travel state correction control processing on the condition that the handle 22 is gripped by the operator OP, the rotation lock of the rear wheel 12 is released by the lock release switch 65, and manual travel is started. The travel state correction control processing is processing for causing the CPU 75 to function as the carriage unit controller 87 shown in FIG. 8, that is, the first acquisition unit 90, the second acquisition unit 91, the third acquisition unit 92, the travel state correction controller 93, and the display controller 94.

First, the first acquisition unit 90 acquires a current position from the current position detection unit 71 as information regarding the travel environment (step ST100). The current position is output from the first acquisition unit 90 to the second acquisition unit 91.

As shown in FIG. 12, the first upper limit value corresponding to the current position acquired by the first acquisition unit 90 is read and acquired from the appropriate travel conditions table 97 by the second acquisition unit 91 (step ST110). The first upper limit value is output from the second acquisition unit 91 to the travel state correction controller 93.

Then, the third acquisition unit 92 acquires a first measurement value from the travel speed measurement unit 72 as information regarding the travel state (step ST120). The first measurement value is output from the third acquisition unit 92 to the travel state correction controller 93.

In FIG. 18, for the convenience of description, the processes of step ST100, step ST110, and step ST120 are separately shown. However, the processes of step ST100, step ST110, and step ST120 are actually performed in parallel. Step ST100 is an example of "first acquisition step" according to the technique of the present disclosure. Step ST120 is an example of "second acquisition step" according to the technique of the present disclosure. Step ST130 is an example of "third acquisition step" according to the technique of the present disclosure.

As shown in FIG. 13, in a case where the travel state does not deviate from the appropriate travel conditions, that is, in a case where the first measurement value is equal to or less than the first upper limit value (NO in step ST130), the travel state correction controller 93 does not perform travel state correction control. On the other hand, as shown in FIG. 14, in a case where the travel state deviates from the appropriate travel conditions, that is, in a case where the first measurement value exceeds the first upper limit value (YES in step ST130), the travel state correction controller 93 performs travel state correction control (step ST140). As shown in FIGS. 14 to 16, the travel state correction control is a control to output a driving control signal, which is for reducing the speed of the carriage unit 10 by the difference between the first upper limit value and the first measurement value within the braking period, to the rear wheel driving unit 13. Step ST140 is an example of "travel state correction control step" according to the technique of the present disclosure.

As shown in FIGS. 17A and 17B, the cause notification screen 100 for providing notification of the cause of the travel state correction control is displayed on the display 26 by the display controller 94 (step ST150). The processing of step ST150 is actually performed in parallel with the processing of step ST140.

The processes from step ST100 to step ST150 are repeated until the hand of the operator OP is separated from the handle 22, the rotation of the rear wheel 12 is locked, and manual travel is stopped (YES in step ST160).

As described above, in the mobile radiographic imaging apparatus 2, the travel state correction controller 93 performs travel state correction control to make a correction to a travel state satisfying the appropriate travel conditions in a case where the travel state of the carriage unit 10 deviates from the appropriate travel conditions. Therefore, it is possible to realize the safer manual travel. For example, there is no possibility that the mobile radiographic imaging apparatus 2 will manually travel through the elevator hall at the speed of 3.0 km/h to hit a person coming out of the elevator. In addition, there is no possibility that the mobile radiographic imaging apparatus 2 will manually travel through the corner at the speed of 2.0 km/h to hit a person coming from the opposite side. Alternatively, there is no possibility that the mobile radiographic imaging apparatus 2 will manually travel through a protruding portion at the speed of 3.0 km/h and break down due to an impact at the time of crossing the protruding portion.

The travel state correction controller 93 does not perform travel state correction control in a case where the travel state of the carriage unit 10 does not deviate from the appropriate travel conditions. For this reason, for the operator OP that manually causes the carriage unit 10 to travel within the appropriate travel conditions, the operation stress is small since the travel state correction control that does not conform to his or her intention is not performed.

The first upper limit value as the appropriate travel conditions is stored in the ROM 73 so as to be associated with each of a plurality of positions set in advance on the floor, on which the carriage unit 10 manually travels, in the form of the appropriate travel conditions table 97. Then, the first acquisition unit 90 acquires a current position as information regarding the travel environment, and the second acquisition unit 91 reads and acquires a first upper limit value corresponding to the current position from the ROM 73. Therefore, it is possible to set the appropriate travel conditions according to the actual state of the floor on which the carriage unit 10 manually travels. In addition, based on the appropriate travel conditions set according to the actual state of the floor in this manner, it is possible to perform travel state correction control that matches the actual state of the floor.

The appropriate travel conditions are the first upper limit value of the travel speed of the carriage unit 10 corresponding to at least one of the width of the travel passage, whether or not the travel passage is a corner, the number of obstacles, the inclination state of the travel passage, or the unevenness state of the travel passage. Then, the third acquisition unit 92 acquires a first measurement value as information regarding the travel state. The travel state correction controller 93 performs travel state correction control in a case where the first measurement value exceeds the first upper limit value. Therefore, the carriage unit 10 can manually travel at a travel speed at which safety can be ensured at each position.

The display controller 94 performs control to display the cause notification screen 100, which shows the cause of performing the travel state correction control, on the display 26. Unless the cause notification screen 100 is displayed in a case where the speed of the carriage unit 10 is reduced by the travel state correction control, the operator OP may be confused by misunderstanding the situation as a failure. However, since the cause notification screen 100 notifies the operator OP of the reason why the travel state correction control is being performed, there is no possibility that the operator OP will be confused. Instead of or in addition to displaying the cause notification screen 100, notification using voice may be provided.

As in an appropriate travel conditions table 105 shown in FIG. 19, a first upper limit value according to the number of obstacles may be set for each time zone.

In FIG. 19, a first upper limit value corresponding to the elevator hall will be described as an example of the first upper limit value according to the number of obstacles. As the first upper limit value corresponding to the elevator hall, two of 1.0 km/h in the time zone of 9:00 to 18:00 and 3.0 km/h in the time zone after 18:00 are set. 9:00 is, for example, the start time of the hospital, and 18:00 is, for example, the reception end time of a visitor. For this reason, it is conceivable that patients, doctors, nurses, and the like enter and exit the elevator hall during rounds, examinations, and the like and patient visitors enter and exit the elevator hall during the time zone of 9:00 to 18:00. On the other hand, in the time zone after 18:00, it is conceivable that the frequency of people going in and out of the elevator hall is low.

Therefore, a relatively slow 1.0 km/h is set as the first upper limit value in the time zone of 9:00 to 18:00, and a relatively fast 3.0 km/h is set as the first upper limit value in the time zone after 18:00.

As described above, by setting the first upper limit value according to the number of obstacles for each time zone, it is possible to perform travel state correction control that further matches the actual state of the floor.

The appropriate travel conditions table 105 shown in FIG. 19 is merely an example. As a mode of setting the first upper limit value according to the number of obstacles for each time zone, the following modes can be adopted. For example, the first upper limit value of the time zone before and after the meal, in which the distribution car moves around, is set to a relatively low value. Alternatively, the first upper limit value in the time zone of 9:00 to 11:00 on holidays that is considered to have a relatively large number of visitors is set to a relatively low value.

Second Embodiment

In a second embodiment shown in FIGS. 20 to 25, information regarding the travel environment is acquired based on the detection result of a detection sensor that detects the travel environment.

Figure 20:
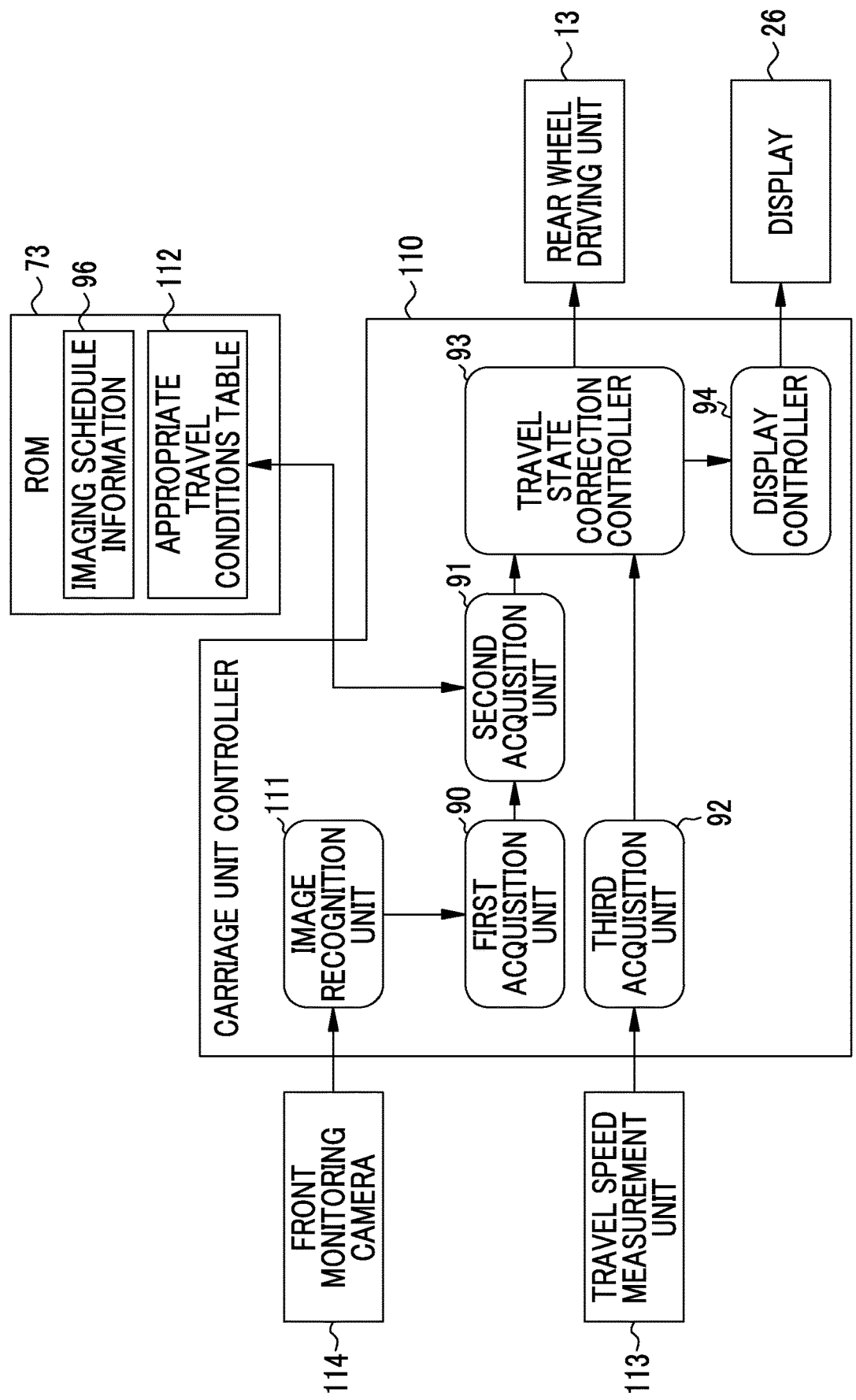
FIG. 20 is a block diagram showing a carriage unit controller of a second embodiment.

In FIG. 20, a carriage unit controller 110 of the second embodiment has an image recognition unit 111. An appropriate travel conditions table 112 is stored in the ROM 73. The third acquisition unit 92 acquires a second measurement value of the travel speed of the carriage unit 10 from a travel speed measurement unit 113. The travel speed measurement unit 113 is the same as the travel speed measurement unit 72 of the first embodiment except that the reference numeral is changed. The second measurement value is the same as the first measurement value of the first embodiment except that the name is changed. The same reference numerals are given to the same components as in the first embodiment described above, and the description thereof will be omitted.

The image recognition unit 111 receives a captured image 115 (refer to FIG. 22) from a front monitoring camera 114. The image recognition unit 111 performs image recognition of the received image, and outputs the image recognition result to the first acquisition unit 90. The first acquisition unit 90 acquires the image recognition result from the image recognition unit 111 as information regarding the travel environment. The front monitoring camera 114 is attached to, for example, the surface of the column unit 16 on the front side of the carriage unit 10, and images the front of the carriage unit 10 that is a movement direction in manual travel. The front monitoring camera 114 is an example of a "detection sensor that detects a travel environment" according to the technique of the present disclosure. The image 115 captured by the front monitoring camera 114 is an example of a "detection result of a detection sensor that detects a travel environment" according to the technique of the present disclosure.

As shown in FIG. 21, the appropriate travel conditions table 112 is a table in which appropriate travel conditions are registered in association with a plurality of travel environments. FIG. 21 shows a total of nine travel environments including a travel passage width less than 2.1 m, a travel passage width of 2.1 in or more, a corner, there is an obstacle, a distance of 3 m from the obstacle, a distance of 2 in from the obstacle, a distance of 1 m from the obstacle, there is a downhill slope in the travel passage, and there is unevenness in the travel passage. In addition, a second upper limit value of the travel speed of the carriage unit 10 is registered as the appropriate travel conditions. More specifically, 1.5 km/h is registered for the travel environment in which the width of the travel passage is less than 2.1 m, 3.0 km/h is registered for the travel environment in which the width of the travel passage is equal to or greater than 2.1 m, and 1.0 km/h is registered for the corner. In addition, 1.0 km/h is registered for the travel environment in which there is an obstacle, 1.0 km/h is registered for the travel environment in which the distance from the obstacle is 3 in, 0.8 km/h is registered for the travel environment in which the distance from the obstacle is 2 m, and 0.5 km/h is registered for the travel environment in which the distance from the obstacle is 1 m. In addition, 1.5 km/h is registered for both the travel environment in which there is a downhill slope in the travel passage and the travel environment in which there is unevenness in the travel passage. Similarly to the first upper limit value, the second upper limit value is registered by the representative of the operator OP or registered based on the first measurement value in a case where the representative of the operator OP actually performs manual travel. As in the case of FIG. 11, also in FIG. 21, the cause of setting the second upper limit value is shown beside the appropriate travel conditions table 112.

Here, "the number of obstacles" is a concept that there are a relatively large or small number of obstacles. Therefore, a case where there is even one obstacle, such as "there is an obstacle" in the travel environment of the appropriate travel conditions table shown in FIG. 21, and a case where there is no obstacle are included in the concept of "the number of obstacles".

As shown in FIG. 22, the situation of the travel passage ahead of the carriage unit 10 is reflected in the image 115 captured by the front monitoring camera 114. The image recognition unit 111 performs image recognition of the image 115 in which the situation of the travel passage is reflected, and derives the width of the travel passage, whether or not the travel passage is a corner, the number of obstacles, the distance from the obstacle, the inclination state of the travel passage, or the unevenness state of the travel passage from the image 115 as image recognition results. Then, the derived image recognition results are output to the first acquisition unit 90 as information regarding the travel environment.

In the image 115 shown in FIG. 22, a travel passage having a width of 2.1 m or more, a downhill slope SL, and a female FM 2 m ahead are reflected. For this reason, the image recognition unit 111 derives, as image recognition results, a travel passage width of 2.1 m or more, there is a downhill slope in the travel passage, there is an obstacle, and a distance of 2 m from the obstacle.

Figure 23:
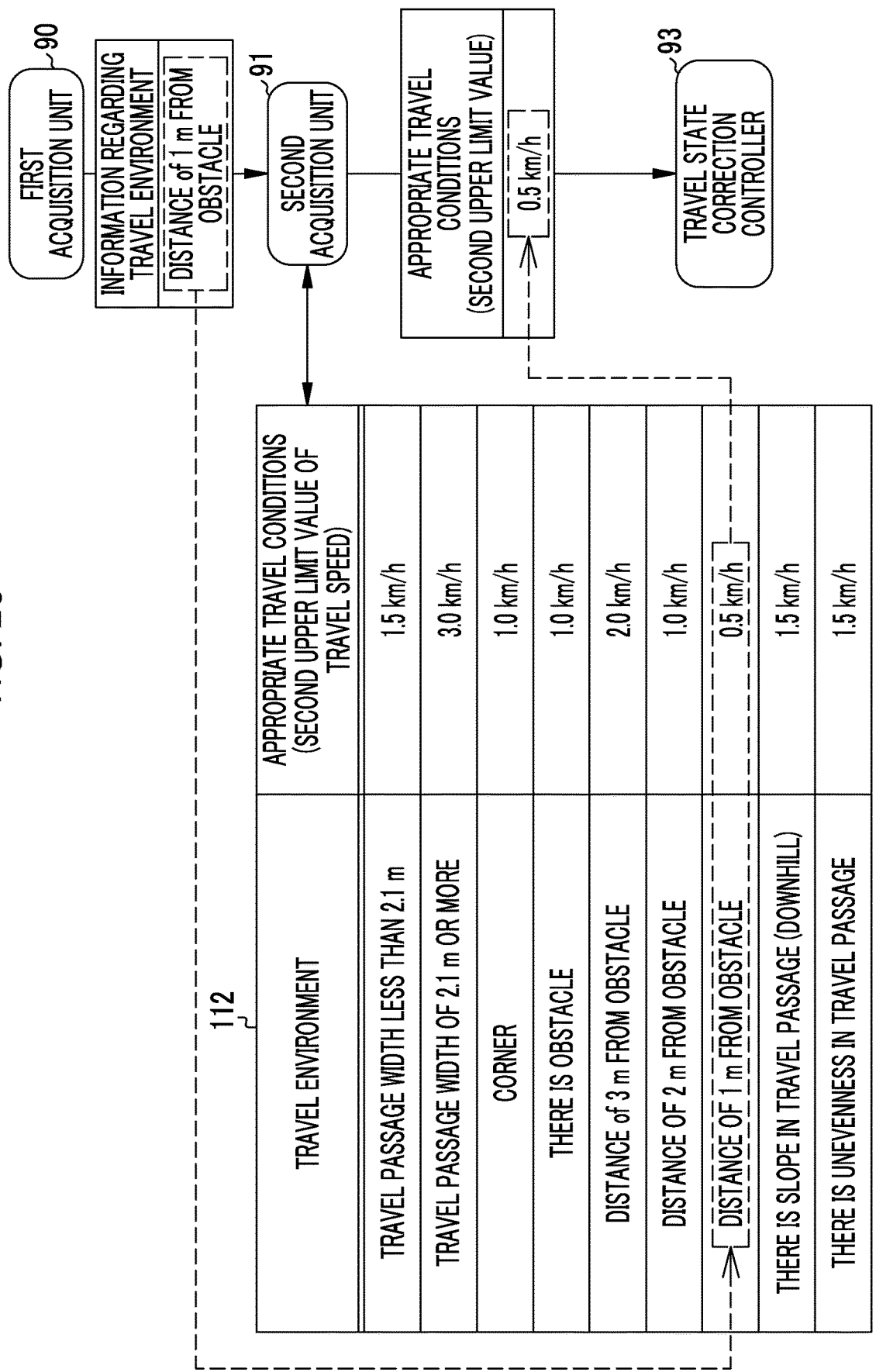
FIG. 23 is a diagram showing the outline of processing of a second acquisition unit in the second embodiment.

In FIG. 23, the second acquisition unit 91 reads and acquires appropriate travel conditions (second upper limit value in the present embodiment), which correspond to the travel environment acquired by the first acquisition unit 90, from the appropriate travel conditions table 97 in the ROM 73. In a case where there are a plurality of travel environments acquired by the first acquisition unit 90, the second acquisition unit 91 reads the strictest appropriate travel conditions among the appropriate travel conditions corresponding to the plurality of travel environments. For example, in a case where the travel environment acquired by the first acquisition unit 90 is a travel passage width of 2.1 m or more, a distance of 3 m from the obstacle, and there is unevenness in the travel passage, the second acquisition unit 91 reads the second upper limit value of 1.5 km/h in the case where there is unevenness in the travel passage, which is the strictest appropriate travel conditions in which the second upper limit value is the lowest.

FIG. 23 illustrates a case where the travel environment acquired by the first acquisition unit 90 is a distance of 1 m from the obstacle. In this case, the second acquisition unit 91 reads and acquires the second upper limit value of 0.5 km/h, which is the appropriate travel conditions corresponding to the distance of 1 m from the obstacle, from the appropriate travel conditions table 112.

Figure 24:
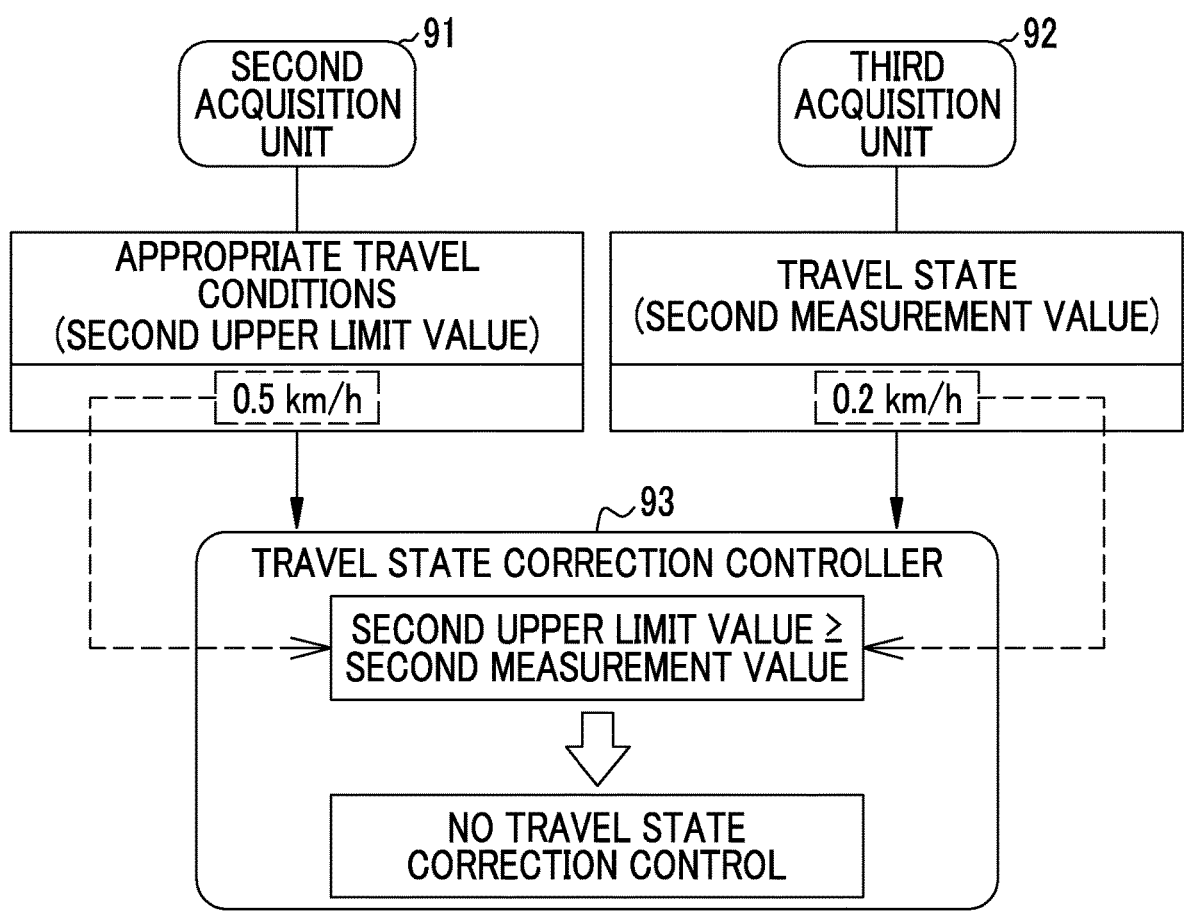
FIG. 24 is a diagram showing the outline of processing of a travel state correction controller in the second embodiment.

As shown in FIG. 24, the travel state correction controller 93 does not perform travel state correction control in a case where the second measurement value acquired by the third acquisition unit 92 is equal to or less than the second upper limit value acquired by the second acquisition unit 91 (second upper limit value 2 second measurement value). FIG. 24 illustrates a case where the second upper limit value from the second acquisition unit 91 is 0.5 km/h and the second measurement value from the third acquisition unit 92 is 0.2 km/h. In this case, since the second measurement value is equal to or less than the second upper limit value, the travel state correction controller 93 does not perform travel state correction control.

Figure 25:
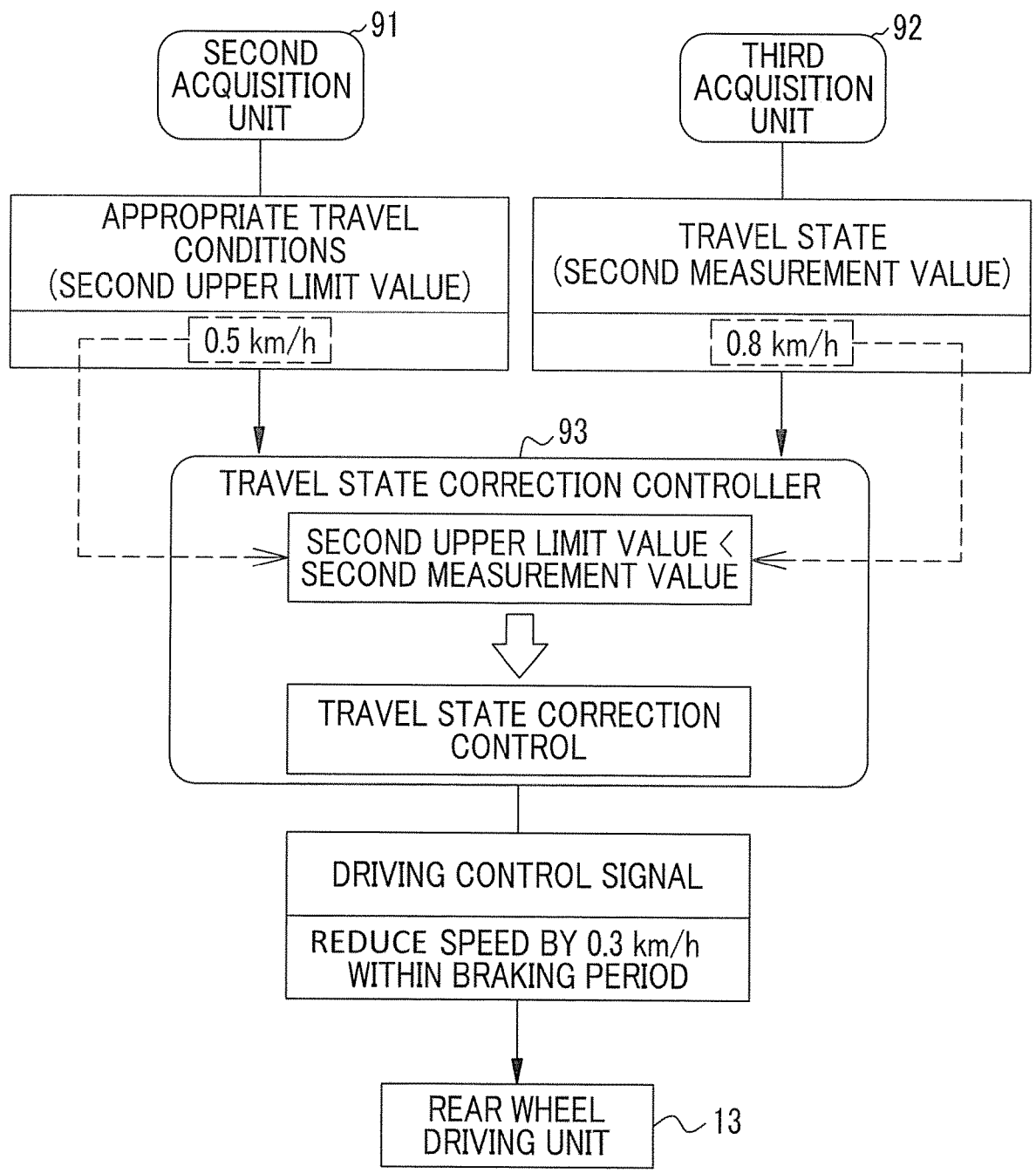
FIG. 25 is a diagram showing the outline of processing of the travel state correction controller in the second embodiment.

On the other hand, as shown in FIG. 25, the travel state correction controller 93 performs travel state correction control in a case where the second measurement value acquired by the third acquisition unit 92 exceeds the second upper limit value acquired by the second acquisition unit 91 (second upper limit value <second measurement value). The content of the travel state correction control is the same as those in the first embodiment.

FIG. 25 illustrates a case where the second upper limit value from the second acquisition unit 91 is 0.5 km/h as in FIG. 24 and the second measurement value from the third acquisition unit 92 is 0.8 km/h. In this case, since the second measurement value exceeds the second upper limit value, the travel state correction controller 93 performs travel state correction control. Since the difference between the second upper limit value and the second measurement value is 0.3 km/h, the travel state correction controller 93 outputs a driving control signal for reducing the speed of the carriage unit 10 by 0.3 km/h within the braking period. By performing such travel state correction control, the travel speed of the mobile radiographic imaging apparatus 2 is reduced from 0.8 km/h to 0.5 km/h.

As described above, in the second embodiment, the first acquisition unit 90 acquires the information regarding the travel environment based on the detection result of the detection sensor that detects the travel environment. More specifically, the first acquisition unit 90 acquires at least one of the width of the travel passage of the carriage unit 10, whether or not the travel passage is a corner, the number of obstacles, the distance from the obstacle, the inclination state of the travel passage, or the unevenness state of the travel passage, as information regarding the travel environment, based on the detection result. The second acquisition unit 91 acquires the second upper limit value of the travel speed of the carriage unit 10 as appropriate travel conditions, and the third acquisition unit 92 acquires the second measurement value of the travel speed of the carriage unit 10 as information regarding the travel state. Then, the travel state correction controller 93 performs travel state correction control in a case where the second measurement value exceeds the second upper limit value. Therefore, as in the first embodiment described above, it is possible to realize the safer manual travel.

In addition, since the detection result of the travel environment detected in real time by the detection sensor is used, it is possible to perform travel state correction control that further matches the actual state of the floor. For example, it is possible to respond to a travel environment that changes from moment to moment, such as obstacles whose positions are not fixed (including a meal distribution car and a cart mounted with thermometers carried by a nurse) or protruding portions suddenly generated by facility construction or the like.

The detection sensor that detects the travel environment is not limited to the illustrated front monitoring camera 114. The distance from the obstacle may be detected using ranging sensors, such as an ultrasound sensor, an infrared sensor, and LIDAR. In addition, the inclination of the travel passage and the unevenness state may be detected using a micro electromechanical system (MEMS) type motion sensor.

Third Embodiment

In a third embodiment shown in FIGS. 26 to 33, travel state correction control is performed based on the meandering amount of the carriage unit 10.

Figure 26:
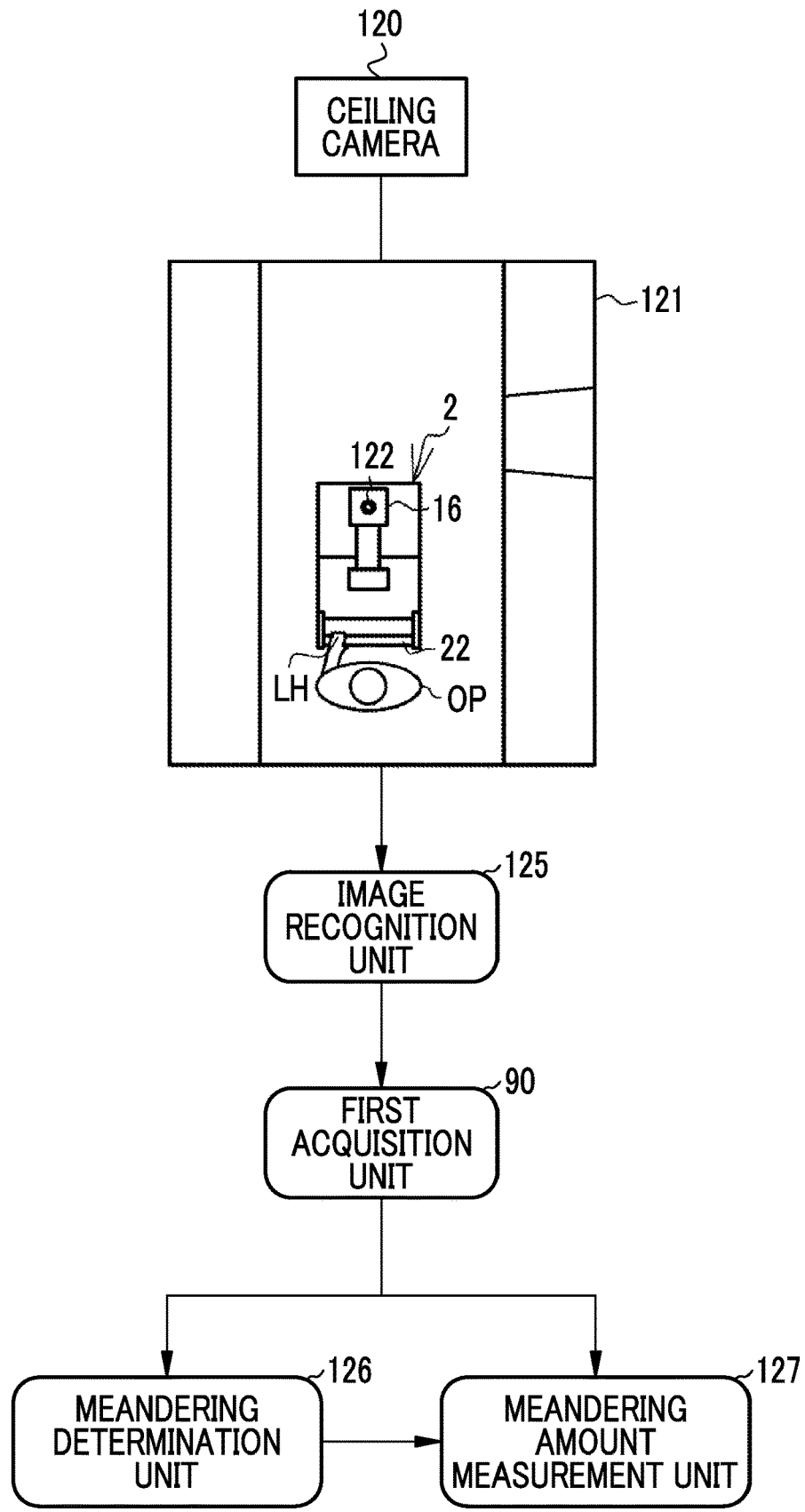
FIG. 26 is a diagram showing the configuration of a third embodiment in which whether or not a carriage unit is meandering and the meandering amount of the carriage unit are derived from an image of a ceiling camera.

In FIG. 26, a ceiling camera 120 is attached to the ceiling of the travel passage to image the travel passage from above. Therefore, the mobile radiographic imaging apparatus 2 that manually travels along the travel passage by the operator OP is reflected in an image 121 captured by the ceiling camera 120. Here, a state is shown in which the operator OP causes the mobile radiographic imaging apparatus 2 to manually travel while gripping the handle 22 with the left hand LH. In the mobile radiographic imaging apparatus 2, a marker 122 is provided at a location where the ceiling camera 120 can capture an image, for example, on the upper surface of the column unit 16.

The ceiling camera 120 is connected to the mobile radiographic imaging apparatus 2 through the communication I/F 70. The ceiling camera 120 outputs the captured image 121 to an image recognition unit 125. The image recognition unit 125 performs image recognition of the marker 122 reflected in the image 121. The image recognition unit 125 outputs the position of the marker 122 in the image 121 to the first acquisition unit 90. The first acquisition unit 90 acquires the position of the marker 122 in the image 121 from the image recognition unit 125 as information regarding the travel environment. The first acquisition unit 90 outputs the acquired position of the marker 122 in the image 121 to a meandering determination unit 126 and a meandering amount measurement unit 127.

Figure 27:
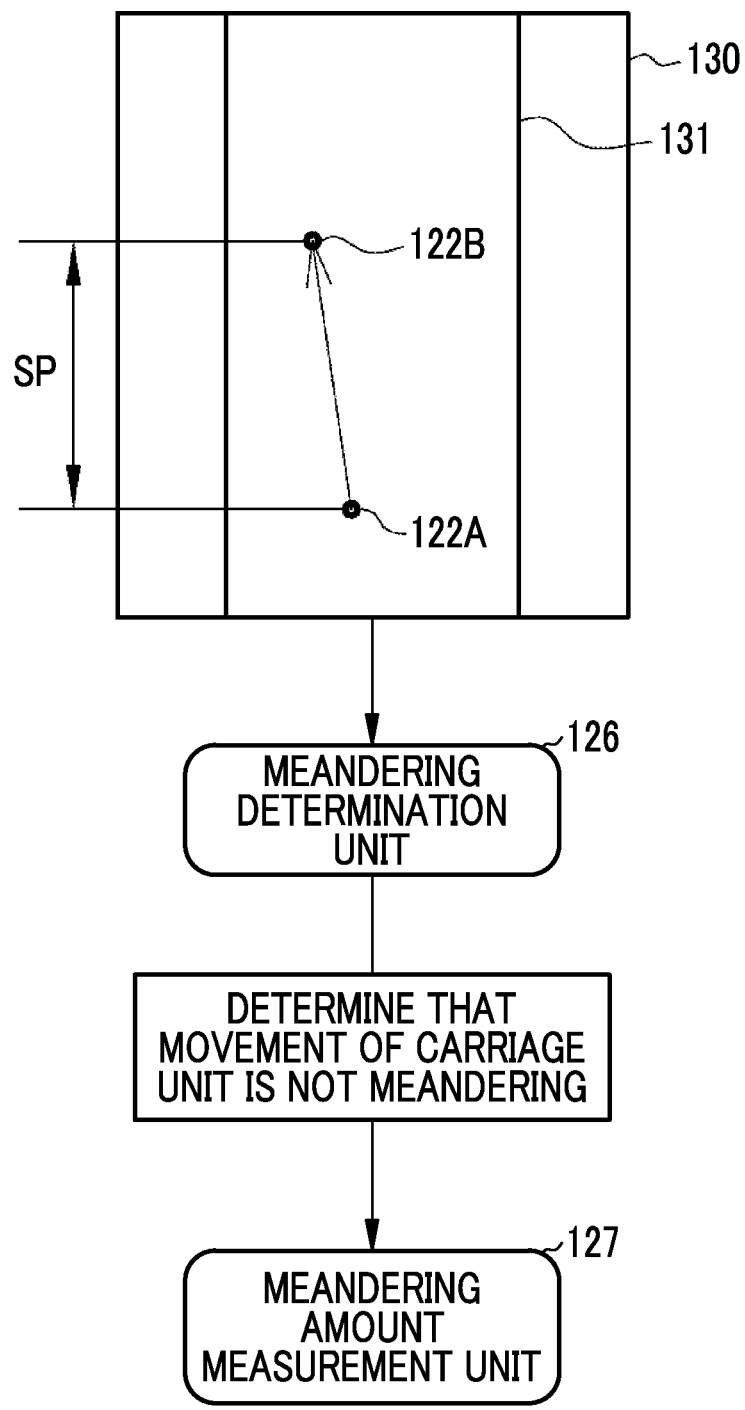
FIG. 27 is a diagram showing the outline of processing of a meandering determination unit.
Figure 28:
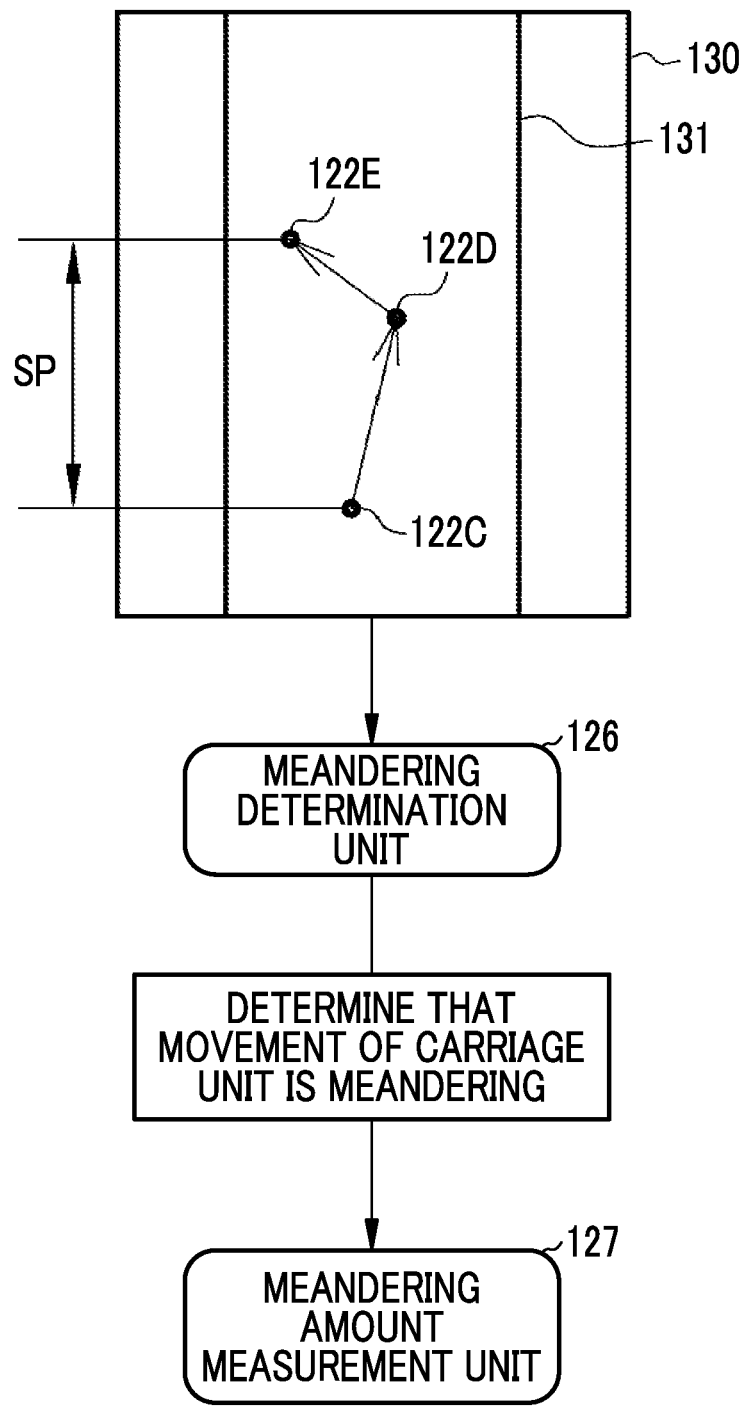
FIG. 28 is a diagram showing the outline of processing of the meandering determination unit.

As in a frame 130 shown in FIGS. 27 and 28, the meandering determination unit 126 determines whether or not the carriage unit 10 is meandering based on the trajectory of the position of the marker 122 in a set period SP. The set period SP is in units of several seconds, for example, five seconds.

In FIG. 27, in a case where the trajectory of the position of the marker 122 in the set period SP is not parallel to an edge 131 of the travel passage but is limited to one direction as indicated by markers 122A and 122B, the meandering determination unit 126 determines that the movement of the carriage unit 10 is not meandering. The meandering determination unit 126 outputs a determination result indicating that the movement of the carriage unit 10 is not meandering to the meandering amount measurement unit 127. In this case, the meandering amount measurement unit 127 does not measure the meandering amount.

On the other hand, in FIG. 28, in a case where the trajectory of the position of the marker 122 in the set period SP is two directions that are not parallel to the edge 131 of the travel passage as indicated by markers 122C, 122D, and 122E, the meandering determination unit 126 determines that the movement of the carriage unit 10 is meandering. The meandering determination unit 126 outputs a determination result indicating that the movement of the carriage unit 10 is meandering to the meandering amount measurement unit 127. In this case, the meandering amount measurement unit 127 measures the meandering amount. In this manner, since it is determined whether or not the carriage unit 10 is meandering based on the trajectory of the position of the marker 122, whether the carriage unit 10 is simply bent due to entering the patient room and the like or the carriage unit 10 is meandering can be distinguished.

Figure 29:
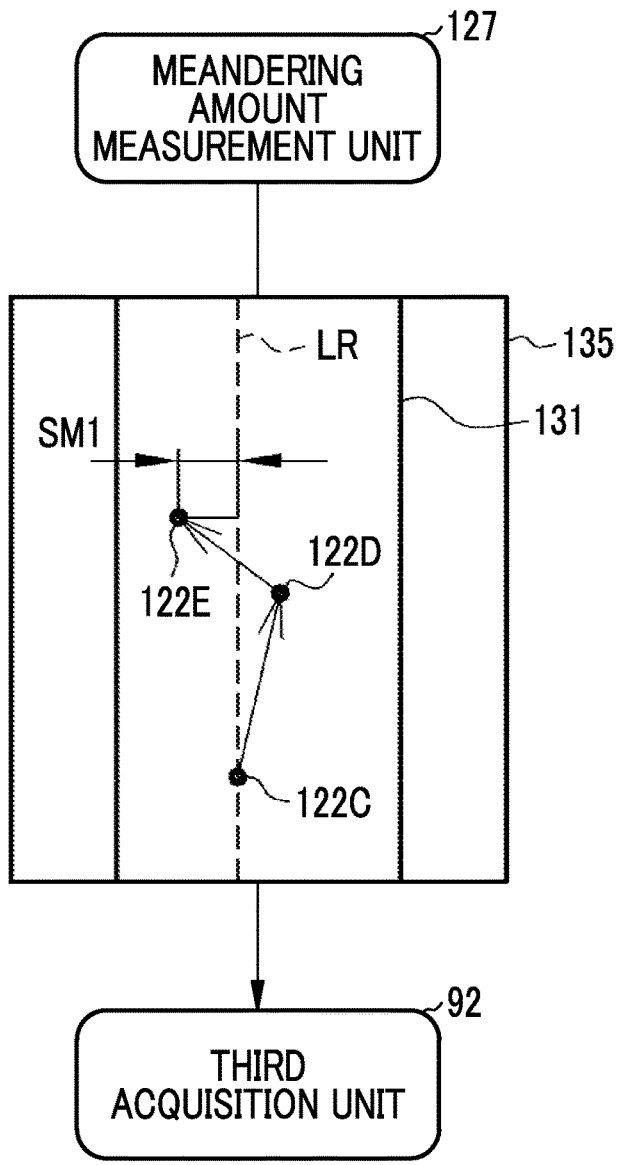
FIG. 29 is a diagram showing the outline of processing of the meandering amount measurement unit.

In FIG. 29, the meandering amount measurement unit 127 derives a measurement value of the meandering amount of the carriage unit 10 based on the position of the marker 122 from the first acquisition unit 90 as shown in a frame 135. More specifically, the meandering amount measurement unit 127 sets a length SM1 of a perpendicular line, which extends from the current position of a marker 122E to a straight route LR, as a measurement value of the meandering amount. The straight route LR is a line that passes through the position of the first marker 122C in the set period SP and is parallel to the edge 131 of the travel passage. The meandering amount measurement unit 127 outputs the measurement value of the meandering amount derived in this manner to the third acquisition unit 92. The third acquisition unit 92 acquires the measurement value of the meandering amount from the meandering amount measurement unit 127 as information regarding the travel state.

Figure 30:
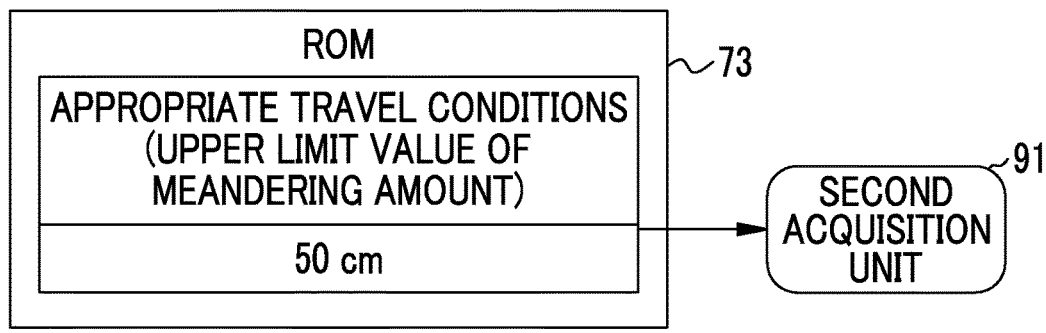
FIG. 30 is a diagram showing the appropriate travel conditions of the third embodiment.

As shown in FIG. 30, in the present embodiment, the upper limit value of the meandering amount of the carriage unit 10 is stored in the ROM 73 as appropriate travel conditions. The second acquisition unit 91 reads and acquires the upper limit value of the meandering amount from the ROM 73.

Figure 31:
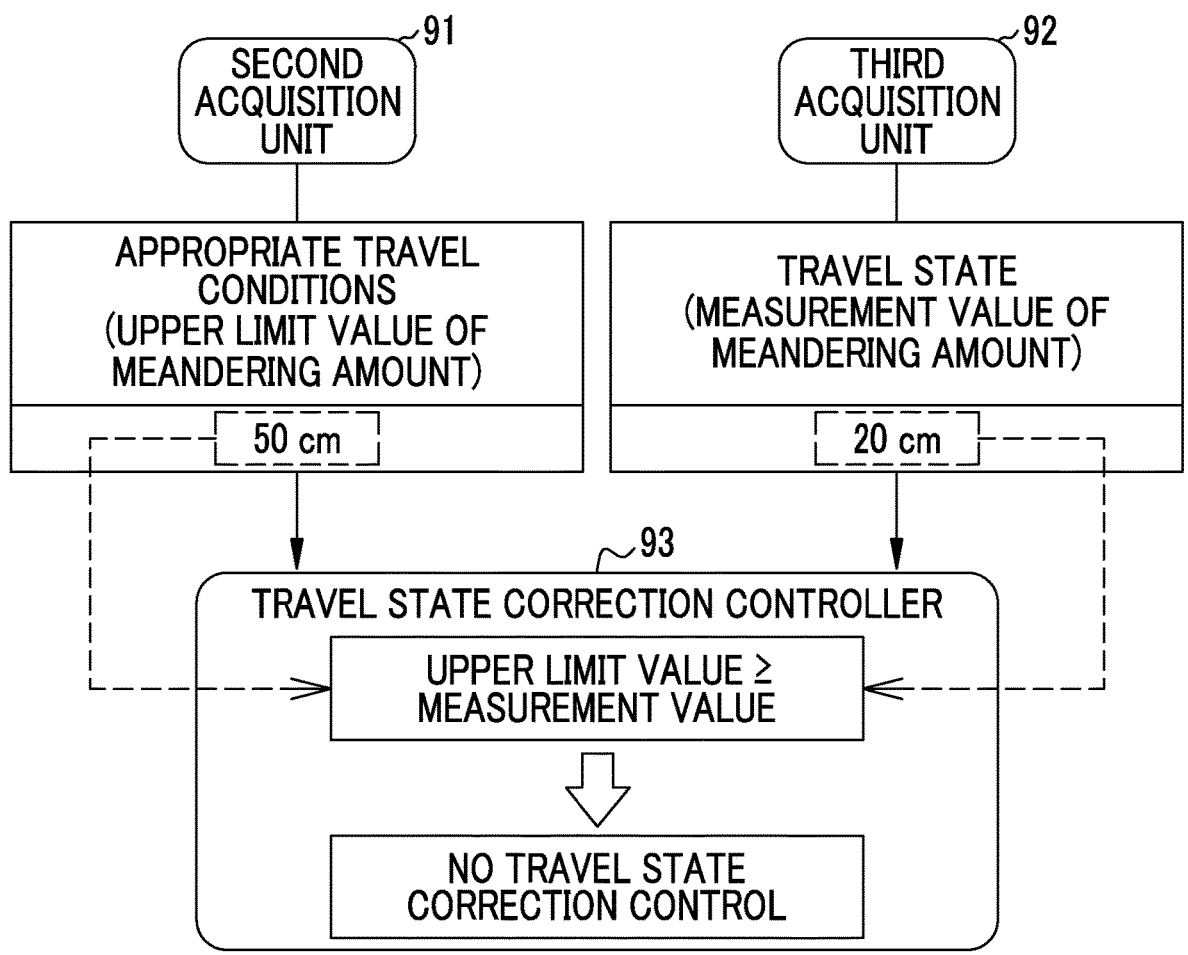
FIG. 31 is a diagram showing the outline of processing of a travel state correction controller in the third embodiment.

As shown in FIG. 31, the travel state correction controller 93 does not perform travel state correction control in a case where the measurement value of the meandering amount acquired by the third acquisition unit 92 is equal to or less than the upper limit value of the meandering amount acquired by the second acquisition unit 91 (upper limit value 2 measurement value). FIG. 31 illustrates a case where the upper limit value of the meandering amount from the second acquisition unit 91 is 50 cm and the measurement value of the meandering amount from the third acquisition unit 92 is 20 cm. In this case, since the measurement value of the meandering amount is equal to or less than the upper limit value of the meandering amount, the travel state correction controller 93 does not perform travel state correction control.

Figure 32:
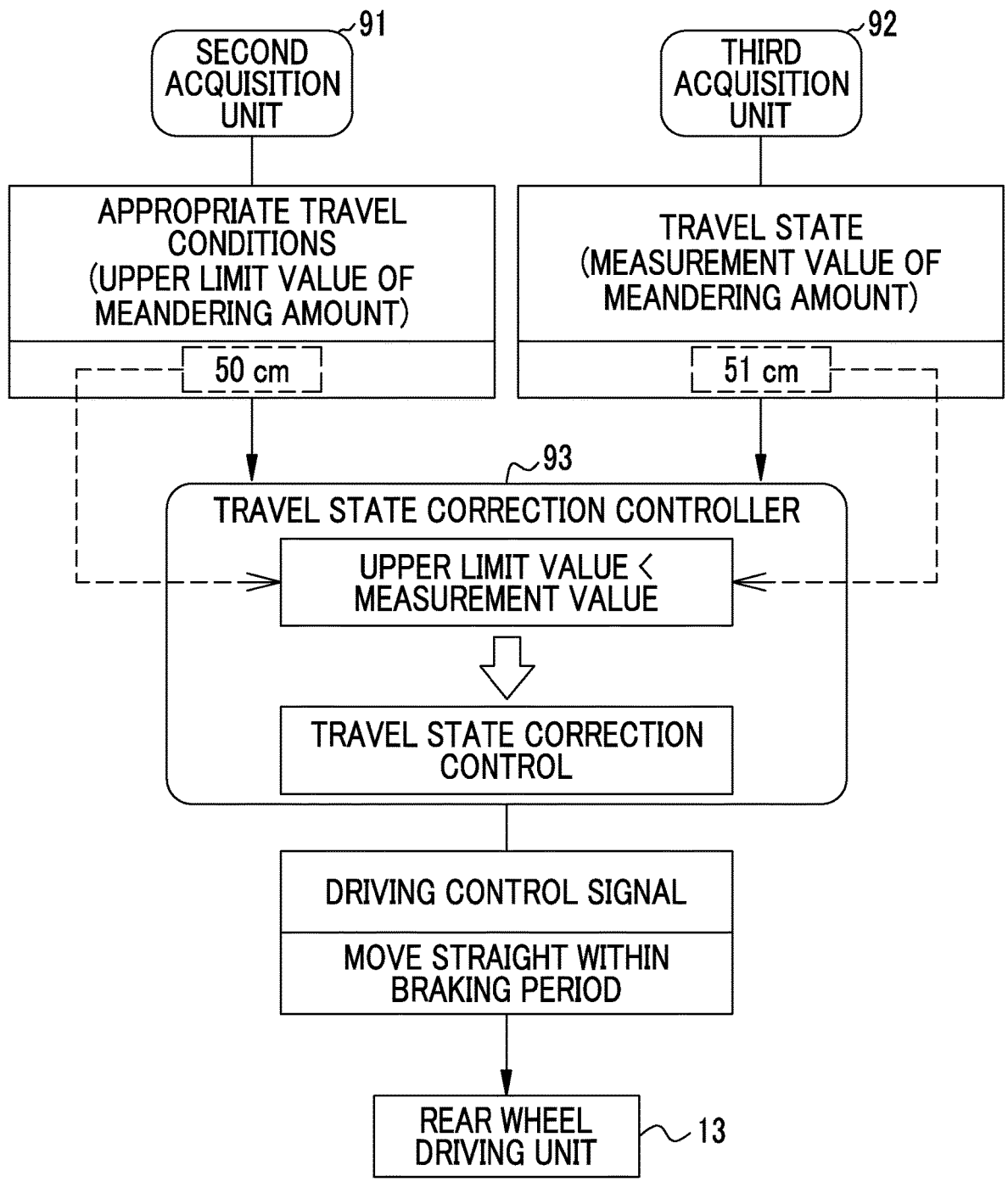
FIG. 32 is a diagram showing the outline of processing of the travel state correction controller in the third embodiment.

On the other hand, as shown in FIG. 32, the travel state correction controller 93 performs travel state correction control in a case where the measurement value of the meandering amount acquired by the third acquisition unit 92 exceeds the upper limit value of the meandering amount acquired by the second acquisition unit 91 (upper limit value <measurement value). The travel state correction controller 93 outputs a driving control signal, which is for making the carriage unit 10 move straight within the braking period, to the rear wheel driving unit 13 as travel state correction control. The braking period is in units of several seconds as in the first embodiment, for example, three seconds.

Specifically, the driving control signal for making the carriage unit 10 move straight is a signal for bending the carriage unit 10 in a direction opposite to the meandering direction. The method of bending the carriage unit 10 is, for example, increasing the rotation speed of the rear wheel 12 on a side opposite to the bending direction or applying a load in a backward direction to the rear wheel 12 on the same side as the bending direction.

Figure 33:
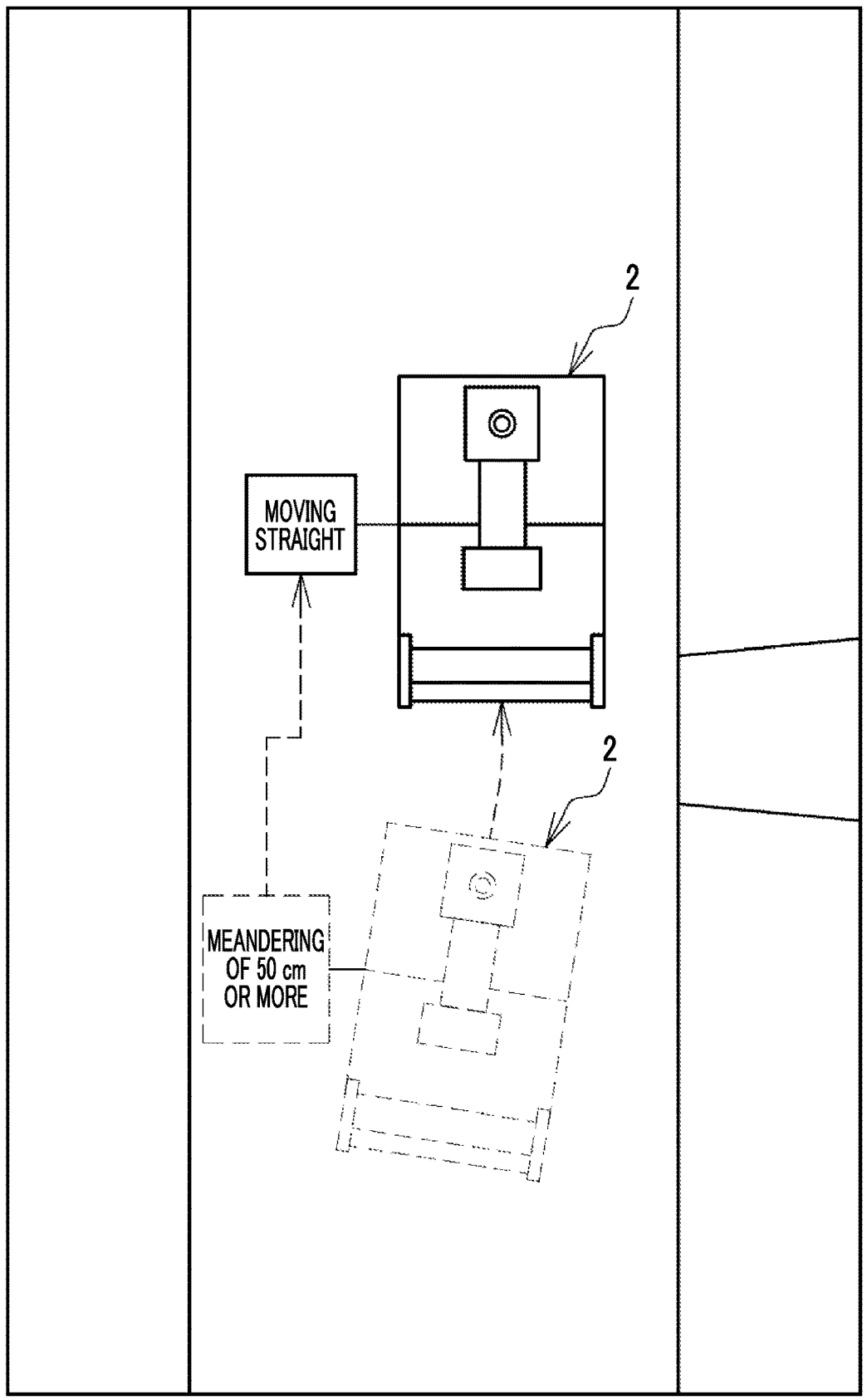
FIG. 33 is a diagram showing how the carriage unit is returned to a straight route by travel state correction control.

FIG. 32 illustrates a case where the measurement value of the meandering amount from the third acquisition unit 92 is 51 cm. In this case, since the measurement value of the meandering amount exceeds the upper limit value of the meandering amount, the travel state correction controller 93 performs travel state correction control. By performing the travel state correction control, as shown in FIG. 33, the mobile radiographic imaging apparatus 2 is returned from the state of meandering of 50 cm or more to the state of moving straight.

Thus, in the third embodiment, the second acquisition unit 91 acquires the upper limit value of the meandering amount of the carriage unit 10 as appropriate travel conditions. The third acquisition unit 92 acquires the measurement value of the meandering amount of the carriage unit 10 as information regarding the travel state. Then, the travel state correction controller 93 performs travel state correction control in a case where the measurement value of the meandering amount exceeds the upper limit value of the meandering amount.

As shown in the image 121 in FIG. 26, for example, in a case where the operator OP operates the handle 22 with one hand because the operator OP holds a load in the other hand, the carriage unit 10 may meander. In addition, the carriage unit 10 may be meandered due to the operator OP's habit, for example, due to the reason that the force of the right hand RH is stronger than that of the left hand LH. However, according to the third embodiment, even in such a situation in which the carriage unit 10 meanders, the meandering amount can be suppressed to be less than the upper limit value. Therefore, it is possible to ensure the safety of manual travel.

The image recognition unit 125 may be provided in a computer other than the mobile radiographic imaging apparatus 2. In this case, the ceiling camera 120 outputs the image 121 to the computer other than the mobile radiographic imaging apparatus 2. In addition, the first acquisition unit 90 acquires the position of the marker 122 in the image 121 from the image recognition unit 125 of the computer other than the mobile radiographic imaging apparatus 2.

The method of measuring the meandering amount is not limited to the above-described method of analyzing the image 121 captured by the ceiling camera 120. For example, the following method may be adopted. That is, a plurality of radio wave transmitters that transmit radio waves of different frequencies are provided at a plurality of locations in the travel passage. A radio wave receiver that receives radio waves from the radio wave transmitter is provided in the mobile radiographic imaging apparatus 2. In the mobile radiographic imaging apparatus 2, a position in the travel passage is specified from the frequency and the strength of the radio wave received by the radio wave receiver. Then, the meandering amount is derived based on the trajectory of the specified position. In addition, a gyro sensor and an acceleration sensor may be used.

Figure 34:
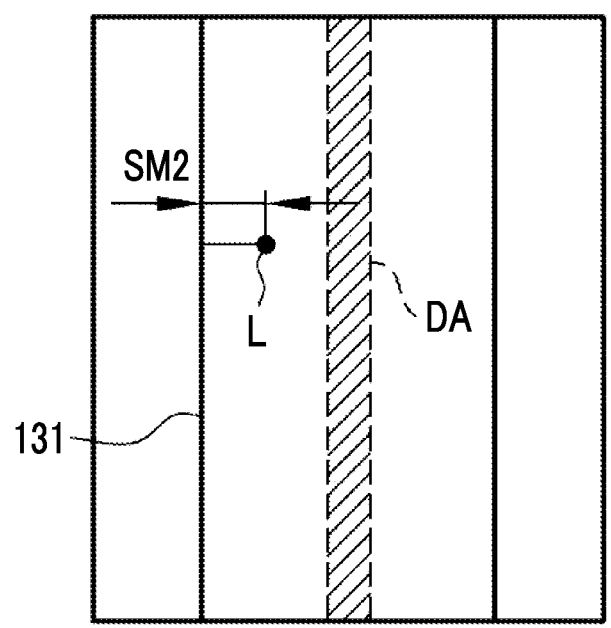
FIG. 34 is a diagram showing another method of measuring the meandering amount.

As shown in FIG. 34, the meandering amount may be measured based on a current position L detected by the current position detection unit 71. That is, a distance SM2 between the current position L and the edge 131 of the travel passage is calculated as the measurement value of the meandering amount. In this case, a travel area DA of the carriage unit 10 in each travel passage is registered in the map information 95 in advance. The travel state correction controller 93 determines whether or not the current position L is within the travel area DA based on the distance SM2 between the current position L and the edge 131 of the travel passage. As illustrated in FIG. 34, in a case where the current position L is not within the travel area DA, the travel state correction controller 93 determines that the current position L is not within the travel area DA and performs travel state correction control. That is, in this case, the width of the travel area DA is an example of the "upper limit value of the meandering amount" according to the technique of the present disclosure.

Alternatively, the distance SM2 between the current position L and the edge 131 of the travel passage may be sampled at predetermined intervals, for example, every one second, and the meandering amount may be measured based on the history of the distance SM2 obtained as a result. In this case, in a case where the variation of the measured meandering amount per unit time, for example, per five seconds exceeds the upper limit value of the meandering amount set in advance, the travel state correction controller 93 performs the travel state correction control.

In each of the above embodiments, only the case where the inclination state of the travel passage is a downhill has been described. However, also in a case where the inclination is an uphill, the travel state correction control may be performed. The travel state correction control in a case where the inclination is an uphill is a control to increase the travel speed to the lower limit value in a case where the measurement value of the travel speed becomes equal to or less than the lower limit of the travel speed.

The first acquisition unit 90, the second acquisition unit 91, and the third acquisition unit 92 may be one acquisition unit.

In each of the embodiments described above, for example, various processors shown below can be used as the hardware structures of processing units that execute various kinds of processing, such as the first acquisition unit 90, the second acquisition unit 91, the third acquisition unit 92, the travel state correction controller 93, the display controller 94, the image recognition units 111 and 125, and the meandering amount measurement unit 127. The various processors include not only the above-described CPU, which is a general-purpose processor that executes software (operation program 80) to function as various processing units, but also a programmable logic device (PLD) that is a processor whose circuit configuration can be changed after manufacture, such as a field programmable gate array (FPGA), and/or a dedicated electric circuit that is a processor having a circuit configuration that is designed for exclusive use in order to execute specific processing, such as an application specific integrated circuit (ASIC).

One processing unit may be configured by one of these various processors, or may be a combination of two or more processors of the same type or different types (for example, a combination of a plurality of FPGAs and/or a combination of a CPU and an FPGA). Alternatively, a plurality of processing units may be configured by one processor.

As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor for realizing the function of the entire system including a plurality of processing units with one integrated circuit (IC) chip. Thus, various processing units are configured by using one or more of the above-described various processors as a hardware structure.

More specifically, as the hardware structure of these various processors, it is possible to use an electrical circuit (circuitry) in which circuit elements, such as semiconductor elements, are combined.

From the above description, it is possible to grasp the invention described in the following supplementary item 1.

Supplementary Item 1

A mobile radiographic imaging apparatus comprising: a carriage unit which has wheels for traveling and on which a main body unit is mounted; a handle that is provided in the main body unit to steer the carriage unit; a wheel driving unit that rotationally drives the wheels to assist manual travel for making the carriage unit travel by an operator's operation on the handle; a first acquisition processor that acquires information regarding a travel environment of the carriage unit; a second acquisition processor that acquires appropriate travel conditions of the carriage unit according to the information regarding the travel environment acquired by the first acquisition processor; a third acquisition processor that acquires information regarding a travel state of the carriage unit in the manual travel; and a travel state correction control processor that performs travel state correction control to make a correction to a travel state satisfying the appropriate travel conditions by controlling the wheel driving unit in a case where the travel state acquired by the third acquisition processor deviates from the appropriate travel conditions acquired by the second acquisition processor.

According to the technique of the present disclosure, it is possible to appropriately combine at least any two of the above-described various embodiments and various modification examples. In addition, it is needless to say that, without being limited to the embodiments described above, various configurations can be adopted without departing from the scope of the present disclosure. In addition, the technique of the present disclosure extends not only to a program but also to a storage medium that stores a program non-temporarily.

The described content and the illustrated content above are detailed descriptions of portions relevant to the technique of the present disclosure, and are merely examples of the technique of the present disclosure. For example, the above descriptions regarding the configurations, functions, operations, and effects are descriptions regarding examples of the configurations, functions, operations, and effects of portions relevant to the technique of the present disclosure.

Therefore, it is needless to say that unnecessary portions may be deleted, new elements may be added, or replacement may be performed for the described content and the illustrated content above without departing from the spirit of the technique of the present disclosure. In addition, in order to avoid complications and facilitate understanding of the portions relevant to the technique of the present disclosure, descriptions regarding common technical knowledge and the like for which descriptions for enabling the implementation of the technique of the present disclosure are not required in particular are omitted.

In this specification, "A and/or B" is synonymous with "at least one of A or B". That is, "A and/or B" may be only A, only B, or a combination of A and B. In addition, in this specification, the same concept as "A and/or B" is applied to a case where three or more things are expressed with "and/or".

All documents, patent applications, and technical standards described in this specification are incorporated in this specification by reference to the same extent as in a case where the incorporation of individual documents, patent applications, and technical standards by reference is described specifically and individually.

What is claimed is:

1. A mobile radiographic imaging apparatus, comprising:
   a carriage unit which has wheels for traveling and on which a main body unit is mounted;
   a handle that is provided in the main body unit to steer the carriage unit;
   a wheel driving unit including a motor that rotationally drives the wheels to assist manual travel for making the carriage unit travel by an operator's operation on the handle; and
   a processor, configured to:
      acquire information regarding a travel environment of the carriage unit;
      acquire, as appropriate travel conditions of the carriage unit, a upper limit value of a travel speed of the carriage unit corresponding to at least one of a width of a travel passage of the carriage unit, whether or not the travel passage is a corner, a number of obstacles that are present in the travel passage to become obstacles to the manual travel, an inclination state of the travel passage, or an unevenness state of the travel passage according to the information regarding the travel environment;
      acquire a measurement value of the travel speed of the carriage unit as information regarding a travel state of the carriage unit in the manual travel; and
      perform travel state correction control to make a correction to the travel state of the carriage unit in the manual travel based on the operator's operation on the handle for satisfying the acquired appropriate travel conditions corresponding to the travel environment of the carriage unit by controlling the wheel driving unit in a case where the travel state deviates from the appropriate travel conditions, wherein the travel state deviating from the appropriate travel conditions includes the measurement value exceeding the upper limit value.

2. The mobile radiographic imaging apparatus according to claim 1,
   wherein the appropriate travel conditions are stored in a storage unit so as to be associated with each of a plurality of positions set in advance on a floor on which the carriage unit manually travels, and the processor is further configured to:

acquire a current position of the carriage unit on the floor as the information regarding the travel environment, and read and acquire the appropriate travel conditions corresponding to the current position from the storage unit.

3. The mobile radiographic imaging apparatus according to claim 1, wherein the upper limit value according to the number of obstacles is set for each time zone.

4. The mobile radiographic imaging apparatus according to claim 1, wherein the processor is further configured to acquire the information regarding the travel environment based on a detection result of a detection sensor that detects the travel environment.

5. The mobile radiographic imaging apparatus according to claim 1, wherein the processor is further configured to:

acquire an upper limit value of a meandering amount of the carriage unit-as other one of appropriate travel conditions, acquire a measurement value of the meandering amount of the carriage unit as the infoi illation regarding the travel state, and perform the travel state correction control in a case where the measurement value of the meandering amount exceeds the upper limit value of the meandering amount.

6. The mobile radiographic imaging apparatus according to claim 1, further comprising:

a display controller that performs control to provide notification of a cause of performing the travel state correction control.

7. The mobile radiographic imaging apparatus according to claim 4, wherein the processor is further configured to acquire at least one of the width of the travel passage of the carriage unit, whether or not the travel passage is a corner, the number of obstacles that are present in the travel passage to become obstacles to the manual travel, the distance from each of the obstacles, the inclination state of the travel passage, or the unevenness state of the travel passage, as the information regarding the travel environment, based on the detection result.

8. An operation method of a mobile radiographic imaging apparatus comprising a carriage unit which has wheels for traveling and on which a main body unit is mounted, a handle that is provided in the main body unit to steer the carriage unit, and a wheel driving unit including a motor that rotationally drives the wheels to assist manual travel for making the carriage unit travel by an operator's operation on the handle, the method comprising:

acquiring infoiiiiation regarding a travel environment of the carriage unit;

acquiring, as appropriate travel conditions, a upper limit value of a travel speed of the carriage unit corresponding to at least one of a width of a travel passage of the carriage unit, whether or not the travel passage is a corner, a number of obstacles that are present in the travel passage to become obstacles to the manual travel, an inclination state of the travel passage, or an unevenness state of the travel passage;

acquiring a measurement value of the travel speed of the carriage unit as information regarding a travel state of the carriage unit in the manual travel; and performing travel state correction control to make a correction to the travel state of the carriage unit in the manual travel based on the operator's operation on the handle for satisfying the acquired appropriate travel conditions corresponding to the travel environment of the carriage unit by controlling the wheel driving unit in a case where the travel state deviates from the appropriate travel conditions, wherein the travel state deviating from the appropriate travel condition includes the measurement value exceeds the upper limit value.

9. A non-transitory computer-readable storage medium storing an operation program of a mobile radiographic imaging apparatus comprising a carriage unit which has wheels for traveling and on which a main body unit is mounted, a handle that is provided in the main body unit to steer the carriage unit, and a wheel driving unit that rotationally drives the wheels to assist manual travel for making the carriage unit travel by an operator's operation on the handle, the operation program causing a computer to:

acquire information regarding a travel environment of the carriage unit;

acquire, as appropriate travel conditions, a upper limit value of a travel speed of the carriage unit corresponding to at least one of a width of a travel passage of the carriage unit, whether or not the travel passage is a corner, a number of obstacles that are present in the travel passage to become obstacles to the manual travel, an inclination state of the travel passage, or an unevenness state of the travel passage;

acquire a measurement value of the travel speed of the carriage unit as information regarding a travel state of the carriage unit in the manual travel; and perform travel state correction control to make a correction to the travel state of the carriage unit in the manual travel based on the operator's operation on the handle for satisfying the acquired appropriate travel conditions corresponding to the travel environment of the carriage unit by controlling the wheel driving unit in a case where the travel state deviates from the appropriate travel conditions, wherein the travel state deviating from the appropriate travel conditions includes the measurement value exceeds the upper limit value.

\* \* \* \* \*